United States Patent
Neumann

(10) Patent No.: US 11,742,069 B2
(45) Date of Patent: Aug. 29, 2023

(54) SYSTEMS AND METHODS FOR GENERATING A NOCICEPTION NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 185 days.

(21) Appl. No.: 17/164,631

(22) Filed: Feb. 1, 2021

(65) Prior Publication Data

US 2022/0246277 A1    Aug. 4, 2022

(51) Int. Cl.
*G16H 20/60*    (2018.01)

(52) U.S. Cl.
CPC .................................. *G16H 20/60* (2018.01)

(58) Field of Classification Search
CPC ...................................................... G16H 20/60
USPC .............................................................. 705/2
See application file for complete search history.

(56) References Cited

U.S. PATENT DOCUMENTS

| | | | |
|---|---|---|---|
| 6,136,795 A | 10/2000 | Florio | |
| 9,055,763 B2* | 6/2015 | Leyer | A61P 1/00 |
| 2005/0177397 A1* | 8/2005 | Kane | G16H 10/20 |
| | | | 705/2 |
| 2008/0026983 A1 | 1/2008 | Gardiner | |
| 2015/0352071 A1 | 12/2015 | Strozier | |

(Continued)

FOREIGN PATENT DOCUMENTS

| | | |
|---|---|---|
| KR | 102022628 B1 | 9/2019 |
| WO | 2015126841 A1 | 8/2015 |

(Continued)

OTHER PUBLICATIONS

Mariangela Rondanelli et al.; Food pyramid for subjects with chronic pain: foods and dietary constituents as anti-inflammatory and antioxidant agents; Journal: Nutrition Research Reviews / vol. 31 / Issue 1/Jun. 2018 (Year: 2018).*

(Continued)

*Primary Examiner* — Hiep V Nguyen
(74) *Attorney, Agent, or Firm* — CALDWELL INTELLECTUAL PROPERTY LAW

(57) ABSTRACT

A system for generating a nourishment program includes a computing device configured to retrieve a nociception parameter, classify the nociception parameter to a nociception grouping, identify, using the nociception grouping, a plurality of nutrition elements, wherein identifying the plurality of nutrition elements includes generating a plurality of nutritional metrics associated with reduction of nociception as a function of the nociception grouping, determining a respective effect of each nutritional metric of the plurality of nutritional metrics on the nociception parameter, calculating at least a nutritional level as a function of the respective effect of each nutritional metric, wherein the at least a nutritional level comprises an amount intended to address the nociception parameter, and identifying the plurality of nutrition elements as a function of the at least a nutritional level, and generate a nociception nourishment program using the plurality of nutrition elements.

16 Claims, 9 Drawing Sheets

(56) References Cited

U.S. PATENT DOCUMENTS

| | | |
|---|---|---|
| 2016/0128961 A1 | 5/2016 | De Leon |
| 2018/0140245 A1 | 5/2018 | Videman |
| 2020/0132699 A1 | 4/2020 | Frantz |
| 2020/0155847 A1 | 5/2020 | Perez |
| 2020/0164209 A1 | 5/2020 | Hogg |
| 2020/0384198 A1 | 12/2020 | Hyde |

FOREIGN PATENT DOCUMENTS

| | | | | |
|---|---|---|---|---|
| WO | WO-2017006313 A2 * | 1/2017 | ............ | A61B 3/112 |
| WO | 2020237048 A1 | 11/2020 | | |

OTHER PUBLICATIONS

Emilie Reber et al. ; Nutritional Risk Screening and Assessment; J. Clin. Med. 2019, 8, 1065; doi:10.3390/jcm8071065 (Year: 2019).*
Journal of Pain Research, 9: p. 1179-1189. doi: 10.2147/JPR. S115068. eCollection 2016, Dec. 8, 2016 (https://www.ncbi.nlm.nih.gov/pmc/articles/PMC5153285/pdf/jpr-9-1179.pdf) By: Manuela De Gregori.

* cited by examiner

SYSTEMS AND METHODS FOR GENERATING A NOCICEPTION NOURISHMENT PROGRAM

FIELD OF THE INVENTION

The present invention generally relates to the field of nutrition planning for alleviating nociception disorders. In particular, the present invention is directed to systems and methods for generating a nociception nourishment program.

BACKGROUND

Efficient systems for targeting nociception-related suffering is stymied from difficulties in adequately sampling the breadth of physiological parameters that relate to nociception-related phenomenon over the lifetime of the subject. Furthermore, systems encounter difficulty in efficiently and properly developing algorithms for targeting the ways in which pain occurs, capturing the amounts of pain, and predicting nociception trajectories from these confounding variables.

SUMMARY OF THE DISCLOSURE

In an aspect, a system for generating a nourishment program for nociception disorders includes a computing device configured to retrieve a nociception parameter related to a subject, classify the nociception parameter to a nociception grouping, identify, using the nociception grouping, a plurality of nutrition elements, wherein identifying the plurality of nutrition elements includes generating a plurality of nutritional metrics associated with reduction of nociception as a function of the nociception grouping, determining a respective effect of each nutritional metric of the plurality of nutritional metrics on the nociception parameter, calculating at least a nutritional level as a function of the respective effect of each nutritional metric, wherein the at least a nutritional level comprises a nutrient amount intended to address the nociception parameter, and identifying the plurality of nutrition elements as a function of the at least a nutritional level, and generate a nociception nourishment program using the plurality of nutrition elements.

In another aspect, a method for generating a nociception nourishment program for nociception disorders includes retrieving, by the computing device, a nociception parameter related to a subject, classifying, by the computing device, the nociception parameter to a nociception grouping, identifying, by the computing device, using the nociception grouping, a plurality of nutrition elements, wherein identifying the plurality of nutrition elements includes generating a plurality of nutritional metrics associated with reduction of nociception as a function of the nociception grouping, determining a respective effect of each nutritional metric of the plurality of nutritional metrics on the nociception parameter, calculating at least a nutritional level as a function of the respective effect of each nutritional metric, wherein the at least a nutritional level comprises a nutrient amount intended to address the nociception parameter, and identifying the plurality of nutrition elements as a function of the at least a nutritional level, and generating, by the computing device, a nociception nourishment program using the plurality of nutrition elements.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a nociception nourishment program. In an embodiment, system includes a computing device configured to retrieve a nociception parameter. Computing device may receive nociception biologic relating to a subject and may generate nociception parameter using a machine-learning model and training data including a plurality of data entries correlating nociception biologics to nociception parameters. Computing device may use at least a nociception parameter to classify a subject to a nociception grouping, which may include a classification of a nociception disorder, including etiology and nutritional deficiency information. Computing device is configured to identify a plurality of nutrition elements by generating a plurality of nutritional metrics, determining a respective effect relating to each nutritional metric, and calculating a nutritional level as a function of the effect. Calculating nutritional levels may include a therapeutic level of nutrient according to the classification of a nociception parameter. Computing device is configured to generate a nociception nourishment program. Generating nociception nourishment program may include generate a linear programming function used to output an ordering of nutrition elements according to a consumption model. In an embodiment, nociception nourishment program may include a nociception nourishment index.

Figure 1:
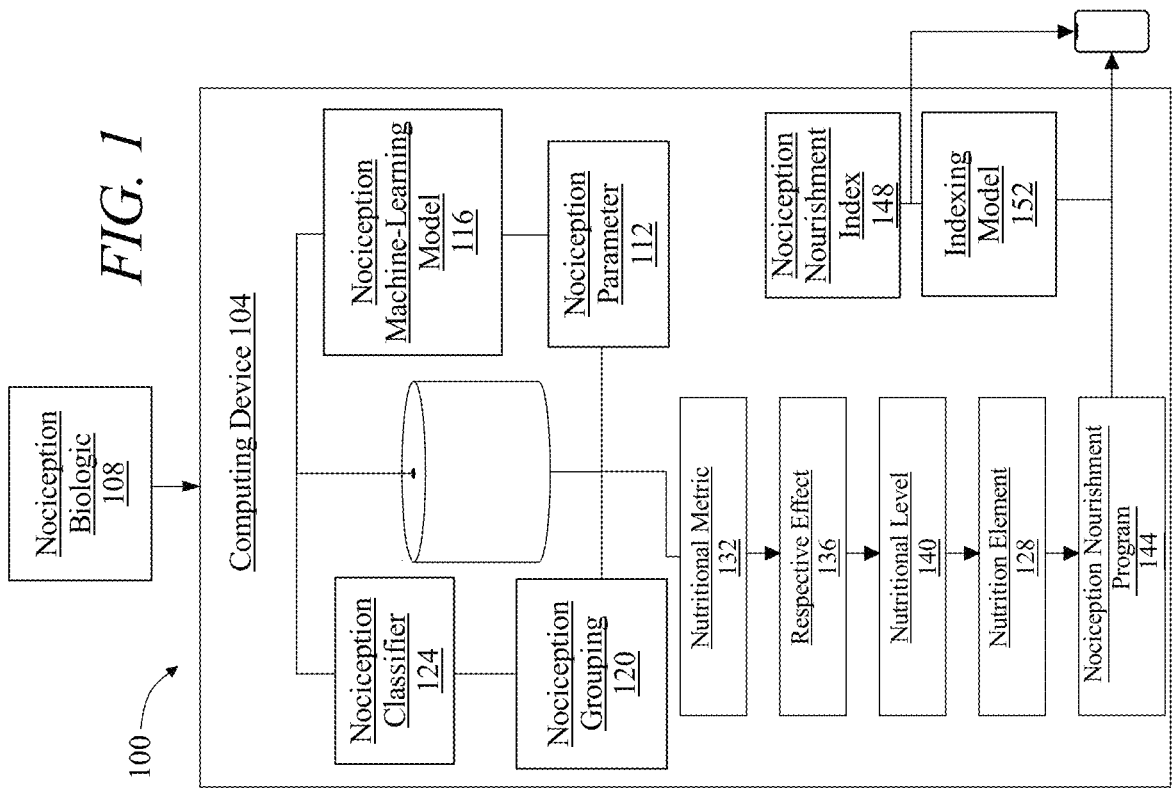
FIG. 1 is a block diagram illustrating a system for generating a nociception nourishment program.

Referring now to FIG. 1, an exemplary embodiment of a system 100 for generating a nociception nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device may be configured to receive at least a nociception biologic relating to a subject. A "nociception biologic," as used in this disclosure, is a datum describing a biological and/or chemical substance or process that is indicative of pain. "Nociception," as used in this disclosure, is a term encompassing a subject's experience of pain and/or discomfort. Nociception may include the neural process(es) of encoding and processing noxious stimuli, such as thermal sensation, pressure and force sensation, painful sensation, discomfort sensation, among other noxious stimuli and/or responses thereof. Nociception biologic 108 may include any biological and/or chemical substance or process that is indicative of and/or relating to the presence of pain in the body. Nociception biologic 108 may include receiving data indicative of biological degradation over the lifetime of the subject, wherein degradation is physiological deterioration over time, as a consequence of biological aging and may provide data regarding some level of pain and/or discomfort for the subject. Nociception biologic 108 may include biological molecules existing within a normal cell, a stressed cell, disease state cell, and/or a specific response of the body indicative of deterioration, pain, and/or aging.

Continuing in reference to FIG. 1, receiving the at least a nociception biologic 108 may include receiving a result of one or more tests relating to the subject. Nociception biologic 108 may include test results of screening and/or early detection of neurodegeneration, joint and muscle deterioration, inflammation, diagnostic procedures, prognostic indicators from other diagnoses, from predictors identified in a medical history, physiological data and/or data relating to biomolecules associated with degradation such as physiological parameters including systolic and diastolic blood pressure, pulse pressure, pulse rate, peak expiratory flow, EKG data; blood metabolites such as homocysteine, creatinine, low-density lipoprotein (LDL), very low density lipoprotein (VLDL), high-density lipoprotein (HDL), triglycerides, fasting glucose, glycosylated hemoglobin (HbA1c); body compositional data including BMI, lean body mass, waist-to-hip ratio; hormonal profile including leptin, adiponectin, testosterone; immunological and disease state indicators such as c-reactive protein, IL-6, fibrinogen, albumin, TNF-α, serum amyloid A, cytomegalovirus, Epstein Barr virus, T cell concentration/ratio, Amyloid B42, Total (t)-Tau, F2-isoprostanes (F2-iso), cortisol, DHEA-S, IGF-1; neurotransmitter concentration and balance such as for norepinephrine, epinephrine; biomarkers of organ function such as cystatin C; indicators of oxidative stress such as reactive oxygen species, superoxide dismutase; genotypic and epigenetic indicators of biological aging such as telomere length; among other data indicative of degradation. Nociception biologic 108 may include a pain level and/or pain marker, for instance as indicated by a symptom such as a marker of acute and/or chronic pain, including for example, pain rated on a pain scale, levels of pain, location of pain, pain palliation and provocation, non-verbal signs of pain such as facial grimacing, writhing, moaning, restlessness, appearing tense, guarding the area of pain and the like. Pain indication may be obtained from one or more test and/or patient exams, including for example a pain assessment, subject self-reporting, physical examination, CT scan, MM, X-ray, and the like.

Continuing in reference to FIG. 1, nociception biologic 108 may include results and or analysis enumerating the identification of nucleic acid sequences. Nociception biologic 108 may include the presentation of single nucleotide polymorphisms (SNPs), mutations, chromosomal deletions, inversions, translocation events, and the like, in genetic sequences. Nociception biologic 108 may include epigenetic factors indicative of rates of degradation such as expression patterns of microRNAs (miRNAs). Nociception biologic 108 may include the consequences of genetic manipulation such as gene silencing on protein expression. Nociception biologic 108 may include hematological analysis including results from T-cell activation assays, abnormal nucleation of white blood cells, white blood cell counts, concentrations, recruitment and localization, and the like, which may be indicative of infection, injury, tissue damage, and/or any other noxious stimuli. Nociception biologic 108 may be received as a function of a subject indicating a prior diagnosis, treatment received, among other data indicated in a medical history, physical assessment, and the like. Nociception biologic 108 may include any symptoms, side effects, and co-morbidities associated with and relating to aging, treatment regimens, recovery from injury and/or illness, and the like. Nociception biologic 108 may be received and/or identified from a biological extraction of a subject, which may include analysis of a physical sample of a subject such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, nociception biologic 108 may include results of biomarker assay(s) that measures objective correlation(s) to the neurobiological process(es) underlying chronic and/or acute pain. For instance, such an assay may reveal a high prevalence of atypical biochemistry in a population of patients exhibiting pain. Abnormal biomarker findings may provide objective support for the role of cytokine-mediated inflammation, oxidative stress, abnormally low production of neurotransmitters, and micronutrient deficiencies in the development or worsening of chronic pain. Panels of functional pain biomarkers may provide novel, objective insight into the underlying causes of pain.

Continuing in reference to FIG. 1, nociception biologic 108 may include pain biomarkers, such as neurotransmitter metabolites. Neurotransmitter metabolites may be biomarkers indicative of pain sensation and signal transduction in the body. Synthesis, packaging, release, and re-uptake of neurotransmitter molecules by neurons are highly regulated. Neurotransmitters may be synthesized from common cellular metabolites (and metabolites from nutrients) by enzymes expressed specifically in neurons using the transmitter. In addition to classical transmitters such as acetylcholine, serotonin, and GABA, a few amino acids act as neurotransmitters. Nociception biologic 108 may include neurotransmitters, neurotransmitter metabolites, and related biomarkers such as include acetylcholine, acetylcholine agonists and/or antagonists, choline acetyltransferase (ChAT), acetylcholinesterase, receptors, pathway enzyme functionality, SNPs, mutations, expression levels, aberrant control, and the like; hologenetic neuron integrity, cholinergic gene expression, presence and concentration of micro RNAs for controlling expression of cholinergic genes, SNPs, mutations, aberrant expression, and the like; GABA and GABAnergic cells, dopamine, serotonin, glutamate, signaling peptides, and the like. Persons skilled in the art, having the benefit of the entirety of this disclosure, will be aware of various additional tests, experimental data, and/or biomarkers that may be used and or received as nociception biologic 108.

Continuing in reference to FIG. 1, nociception biologic 108 may be received by computing device 104 via the subject and/or a secondary source. Secondary source may include another individual such as a physician, lab technician, nurse, caretaker, psychologist, dietician, strength coach, physiologist, guardian, and the like. Nociception biologic 108 may be received as raw data from a wearable device and/or physiological sensor intended to gather data relating to a subject experiencing pain and/or discomfort, such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like. Nociception biologic 108 may be received via a web browser and the Internet. Nociception biologic 108 may be received via a database such as a NOSQL database, as described in further detail below.

Continuing in reference to FIG. 1, nociception biologic 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, nociception biologic 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, nociception biologic 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Nociception biologic 108 training data may alternatively or additionally be implemented using a distributed data storage protocol and/or data structure, such as a distributed hash table and the like. Nociception biologic 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of nociception biologics may be stored, retrieved, organized, and/or reflect data and/or records as used herein, as well as categories and/or populations of data consistent with this disclosure.

Continuing in reference to FIG. 1, computing device is configured to retrieve a nociception parameter related to the subject. A "nociception parameter," as used in this disclosure, is a profile that captures a level of nociception biologic 108 of a subject as it relates to experiencing nociception. Nociception parameter 112 may include at least a relative amount of pain in the subject. Nociception parameter 112 may include a rate of nociception, wherein the level of pain and/or discomfort is a relative level compared to a theoretical level of according to what is scientifically achievable for an individual, wherein the level of pain and/or discomfort may change and be tracked and may be provided an objective numerical value. Such a nociception parameter 112 may include a function, or a series of values, plotted as a function of time which describe a level of pain and/or discomfort in a subject according to, for instance neurotransmitter metabolites, nutritional deficiency level, among other nociception biologics 108. Nociception parameter 112 may include an amount of nociception biologic 108 as it relates to a threshold value, for instance and without limitation, a range of values of nociception biologic 108 in a cohort of healthy subjects. Nociception parameter 112 may include an arbitrary numerical value which is assigned according to a scoring function which may be derived by, for instance and without limitation, a machine-learning model which assigns a numerical value to the parameter according to a theoretical maximal value, minimal value, wherein the scoring incrementation is generated as a function of the range. Nociception parameter 112 may include biological degradation such as physiological deterioration in the subject which may contribute to pain and/or discomfort, for instance and without limitation, joint degeneration, inflammation, neurodegeneration, and the like.

Continuing in reference to FIG. 1, nociception parameter 112 may include a quantitative metric that encapsulates a nociception biologic 108 in the subject. For instance and without limitation, a current state of pain may include a nociception biologic 108 that enumerates a current propensity for developing a neurodegenerative disease such as Alzheimer's disease, dementia, Parkinson's disease, among other neurodegenerative disorders, based on advanced physiological deterioration indicative a particular of nociception biologic 108, such as tau protein expression, presence of α-synuclein plaques, Lewy bodies, and the like, which has manifest as pain, tingling, restlessness, discomfort, non-receptiveness to pain management medications, and the like. Nociception parameter 112 may include a parameter which indicates a potential to develop future nociception disorder.

Continuing in reference to FIG. 1, nociception parameter 112 may include a current state of pain disorder such as a numerical value communicating a current level of pain. Current state may include "no nociception disorder". In individuals harboring no obvious disorder, a current state of pain may include a tissue, organ, pain category, and the like, with which the subject may most closely be classified, or have a likelihood of developing in the future, especially according to the presence of mutation, SNPs, family history, among other nociception biologic 108 that may be used to indicate a future nociception disorder. Nociception parameter 112 may be biologic-specific, for instance and without limitation, a numerical value for each of 100+ types of nociception biologic 108 categories, where each numerical value communicates a likelihood that a nociception biologic 108 relates to a particular pain disorder, for instance as the nociception biologic 108 relates to a 'healthy range'.

Continuing in reference to FIG. 1, nociception parameter 112 may include qualitative and/or quantitative summarization of the presence of symptomology, development of pain disorder, biomarkers indicative of pain, current rates of pain and/or discomfort, lifetime risk associated with the current nociception biologic 108, biomarkers classified to subcategories, and the like. Nociception parameter 112 may include qualitative determinations, such as binary "yes"/ "no" determinations for particular degradation types, "normal"/"abnormal" determinations about the presence of and/ or concentration of nociception biologics 108, for instance as compared to a normalized threshold value of a biomarker among healthy adults. Nociception parameter 112 may include a plurality of nociception parameters, wherein nociception parameters are quantitative determinations such as a "nociception nourishment index", which may include any metric, parameter, or numerical value that communicates a level of pain according to nutritional integrity, symptoms, among other nociception biologics 108. Nociception parameter 112 may include nociception parameters that are mathematical expressions relating the current degradation state.

Continuing in reference to FIG. 1, computing device 104 may retrieve nociception parameter 112 from a database. Database may be implemented, without limitation, as a relational database, a key-value retrieval database such as a NOSQL database, or any other format or structure for use as a database that a person skilled in the art would, upon the benefit of this disclosure in its entirety, may recognize as suitable upon review of the entirety of this disclosure. Database may include a degradation program database, as described in further detail below. Alternatively or additionally, database may be implemented using a distributed data storage protocol and/or data structure, such as a distributed hash table and the like. Database may include a plurality of data entries and/or records, as described herein. Data entries for nociception parameter 112 may be flagged with or linked to one or more additional elements of information, which may be reflected in data entry cells and/or in linked tables such as tables related by one or more indices in a relational database.

Continuing in reference to FIG. 1, retrieving nociception parameter 112 may include a process of searching for, locating, and returning nociception parameter 112 data. For example, nociception parameter 112 may be retrieved as documentation on a computer to be viewed or modified such as files in a directory, database, and the like. In non-limiting illustrative embodiments, computing device 104 may locate and download nociception parameter 112 via a web browser and the Internet, receive as input via a software application and a client device, and the like.

Continuing in reference to FIG. 1, retrieving nociception parameter 112 may include receiving data via a graphical user interface. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the subject and accept input from the subject. Graphical user interface may accept input, wherein input may include an interaction (such as a questionnaire) with a client device. A client device, as described in further detail below, may include computing device 104, a "smartphone," cellular mobile phone, desktop computer, laptop, tablet computer, internet-of-things (TOT) device, wearable device, among other devices. Client device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. Client device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Continuing in reference to FIG. 1, computing device 104 is configured to classify the nociception parameter 112 to a nociception grouping. A "nociception grouping," as used in this disclosure, is a determination about a cause and/or contributing factor concerning a current pain state of a subject as a function of a classification of the subject according to a subset of a plurality of subjects. Nociception grouping 120 may include a designation of a physiological degradation type which relates to some level and/or cause of pain and/or discomfort. Nociception grouping 120 may include tissue, organ, and/or biological system designation such as "kidney damage", "heart condition", "peripheral nervous system degradation", "arthritis", and the like, which may be the underlying cause of the pain and/or discomfort. Nociception grouping 120 may include a designation regarding a pain type that may not involve a particular tissue such as "acute pain", "chronic pain", "opiate insensitive pain", "opiate receptive pain", "visceral pain", "somatic pain", "neuropathic pain", and the like. Nociception grouping 120 may include pathological, histological, and/or clinical classification identifiers such as "pain rating index (PRI) of 2.5", "numerical rating scale (NRS) score range of 6-9", "myelin sheath thinning", "visual analogue scale (VAS) measurement of 65 mm", and the like. Nociception grouping 120 may include identifiers associated with disorders, conditions, symptoms, and the like, which may correspond with categorization. Nociception grouping 120 may include a predictive classification, where a subject such as a healthy young adult, does not harbor nociception biologic(s) 108 indicative of obvious current pain but may include data that indicates a nociception grouping 120 with which they may be most closely categorized to, for instance from muscle pain, pulling a muscle, joint pain, or other acute soft tissue injury from exercise. For instance, a family history of neurodegeneration as a function of aging due to a combination of epigenetic elements, lifestyle factors, and long-term nutritional impacts, may classify an individual in "neuropathic pain" nociception grouping 120, despite not currently exhibiting any symptomology or other loss of neurological integrity. In such an example, nourishment program paradigm may be focused on prevention of developing that anticipated myopathy, wherein nutrition may act as a prophylaxis. Nociception parameter 112 may have associated with it an identifier, such as a label, that corresponds to a nociception grouping 120. Nociception grouping 120 may be stored and/or retrieved from a database.

Still referring to FIG. 1, retrieving the nociception parameter 112 related to the subject may include training a nociception machine-learning model with training data including a plurality of data entries correlating nociception biologics 108 to nociception parameters 112. Computing device 104 may generate the nociception parameter 112 as a function of the nociception machine-learning model and the at least a nociception biologic 108. Nociception machine-learning model 116 may include any machine-learning process, algorithm, and/or model as performed by machine-learning module, described in further detail below. Generating nociception parameter 112 as a function of training data and a machine-learning model may be performed, without limitation, as described in Ser. No. 17/000,929, filed Aug. 24, 2020, titled "METHOD OF AND SYSTEM FOR IDENTIFYING AND AMELIORATING BODY DEGRADATIONS," the entirety of which is incorporated herein by reference. Particular body degradations may be related to generation of pain and/or discomfort in the subject. Nociception machine-learning model 116 may be generated an output of nociception parameter 112 from nociception biological 108, which includes an objective enumeration of pain in the subject. From such a nociception parameter 112 a diagnosis regarding the 'type' or 'category' of pain disorder, and finally a relationship between the nociception biologic 108 and the pain that is experienced may be enumerated in nociception parameter 112 according to the model. Relationships observed in training data to enumerate body degradation for nociception parameter 112 may be used to determine cross-body degradations, wherein degradation from one instance may be statistically related to pain/or discomfort for which no directly observable data exists, for instance and without limitation, as described in Ser. No. 17/000,973, filed Aug. 24, 2020, titled "A METHOD OF AND SYSTEM FOR IDENTIFYING AND ENUMERATING CROSS-BODY DEGRADATIONS," the entirety of which is incorporated herein by reference. In such an instance, degradation in joints may relate to joint pain, but secondary pain which originates from a secondary location may be attributed to the joint pain according to a relationship identified in cross-body degradation. Such a cross-body pain relationship may include referred pain, for instance where physiological distress (degradation) in an organ such as the heart, gallbladder, and the like, may manifest as 'referred pain' elsewhere in the body.

Continuing in reference to FIG. 1, training data for nociception machine-learning model 116 may include nociception biologics 108 organized into training data sets, as described herein, including results from biological extraction samples, health state questionnaires regarding symptomology, medical histories, physician assessments, lab work, neurotransmitter metabolites, nutritional state data, and the like. Training data may be retrieved from a database, as described in further detail below. Nociception machine-learning model 116 training data may originate from the subject, for instance via a questionnaire and a user interface with computing device 104, for subject to provide medical history data and/or symptoms. Receiving nociception parameter training data may include receiving whole genome sequencing, gene expression patterns, and the like, for instance as provided by a genomic sequencing entity, hospital, database, the Internet, and the like. Training data may include raw data values recorded and transmitted to computing device 104 via a wearable device and/or physiological sensor data which may be used for determining if a subject tis experiencing pain and/or discomfort, for instance and without limitation, capturing heart rate, pulse, breathing rate, bioimpedance data relating to swelling and/or water retention, blood pressure, blood monitoring for sugar, vitamins, electrolytes, trace minerals, volatile carbon compounds (VOCs) on the breath, and the like. Training data may originate from an individual other than subject, including for instance a physician, lab technician, nurse, dietician, strength coach, psychologist, and the like. Training data may be retrieved from a database, as described in further detail below. Training data may be retrieved by computing device for instance for instance via a web browser and the Internet, such as via a telemedicine platform, data repository, pain monitoring application, and the like. It is important to note that training data for machine-learning processes, algorithms, and/or models used within system 100 herein may likewise originate from any source described for nociception machine-learning model 116 training data.

Continuing in reference to FIG. 1, nociception machine-learning model 116 may include any machine-learning algorithm such as K-nearest neighbors algorithm, a lazy naïve Bayes algorithm, among other algorithms, machine-learning process such as supervised machine-learning, unsupervised machine-learning, or method such as neural nets, deep learning, and the like. Nociception machine-learning model 116 may be trained to derive an equation, function, series of equations, or any mathematical operation, relationship, or heuristic, that can automatedly accept an input, such as nociception biologic(s) 108, and correlate, classify, or otherwise calculate an output, such as nociception parameter(s) 112. Nociception machine-learning model 116 may derive individual functions, derived for unique relationships observed from the training data for each nociception biologic 108, or combinations thereof. In non-limiting illustrative examples, training data may include numerical data involved in a variety of physiological tests, as described above, may be retrieved from a database, such as a repository of peer-reviewed research (e.g. National Center for Biotechnology Information as part of the United States National Library of Medicine), and the nociception machine-learning model 116 may derive an algorithm which determines an average and statistical evaluation (mean±S.D.) derived from the trained data, across which the subject's nociception parameters 112 may be compared. In such an example, nociception machine-learning model 116 may derive an algorithm according to the data used to derive the average and statistical evaluation changes as a function of the subset of data to which the subject is to be compared, for instance and without limitation, based on differentiating factors such as age, fitness level, nutrition deficiency, symptomology, past diagnoses, and the like.

Continuing in reference to FIG. 1, as pathological measurements of pain and/or discomfort may be oftentimes measured by subjective means, nociception parameter 112 may be generated such that it combines nociception biologic 108 and/or pathological, histological, and/or clinical classification identifiers to arrive at more objective parameters to gauge pain in a subject. Subjective means for measuring pain may include the visual analogue scale (VAS) which is a 100 mm line along which a subject indicates a relative amount of pain and/or discomfort; numerical rating scale (NRS) which may include an 11-point scale from 0-10 along which the subject places their current status; the Leeds Assessment of Neuropathic Symptoms and Signs (LANSS) pain scale, the Douleur Neuropathoique en 4 questions (DN4), the McGill Pain Questionnaire (MPQ) including 20 subgroups of words for describing sensory and their evaluation of intensity, among other subjective tests. Such subjective means for measuring pain may relate relative intensities in the form of subjective numerical scales, as well as information regarding sensation such as thermal qualities, pain radiation, 'stabbing pains', and the like, as experienced by the subject. Nociception machine-learning model 116 may relate training data including subjective means correlated to nociception biologics 108 to identify relationships between subjective means and biologics. Such relationships may be used to derive equations, functions, and other mathematical relationships which may identify outliers, a scoring and/or weighting function to place on subjective means to relate them to their true biological significance, and the like. In this way, nociception machine-learning model 116 may output nociception parameter 112 which includes an objective, quantitative measure of pain in the subject. Nociception parameter 112 may include a combination of a subjective means as it may be corroborated and/or cross-referenced to nociception biologic(s) 108 relating to the subject form which the subjective means was obtained.

Continuing in reference to FIG. 1, classifying the nociception parameter 112 to a nociception grouping 120 may include training a nociception classifier using a nociception classification machine-learning process and training data including a plurality of data entries of nociception parameter data from a subset of categorized subjects. A "nociception classifier," as used in this disclosure, is a machine-learning classifier that sorts nociception parameter(s) 112 to a nociception grouping 120. Nociception classifier 124 is generated by a nociception classification machine-learning process, which may include any machine-learning algorithm, process, and/or model described herein performed by a machine-learning module, as described in further detail below. Nociception classification machine-learning process may generate nociception classifier 124 using training data. A classifier may include a machine-learning model, such as a mathematical model, neural net, or program generated by a machine learning algorithm known as a "classification algorithm," as described in further detail below. Nociception classifier 124 may sort inputs, such as nociception parameter 112, into categories or bins of data, such as classifying the data into nociception grouping 120, outputting the bins of data and/or labels associated therewith.

Continuing in reference to FIG. 1, training data for nociception classifier 124 may include a set of nociception biologics 108 as it relates to classes of degradation types, organ and/or tissue types, ability types, and the like. Alternatively or additionally, training data may include a set of nociception parameters 112 as it matches to such classes. For instance and without limitation, training data may include ranges of nociception biologics 108 as they correlate to various degrees of neurodegeneration as it relates to neuropathic pain, chronic pain, acute pain, and the like, wherein the varying degrees of pain may be enumerated by nociception parameter 112. Such training data may include nociception biologics 108 (and/or nociception parameters 112) as it relates to nociception grouping 120 for subsets of a plurality of subjects, segmented according to subject characteristics such as smoking, alcohol consumption, exercise, dietary patterns, nutritional deficiency, age, sex, ethnicity, and the like. Training data may be used by classification machine-learning process to train nociception classifier 124 to derive relationships present in the data that may result in a machine-learning model that automatically classifies a subject to a nociception grouping 120 as a function of their nociception parameter(s) 112. Training data may originate from any source described herein, for instance retrieved from a database, retrieved via a web browser and the Internet, peer-reviewed research repository, clinical data, subject input data, wearable device, physiological sensor, medical history data, and the like.

Continuing in reference to FIG. 1, nociception classifier 124 may be configured to output at least a datum that labels or otherwise identifies a set of data that are clustered together, found to be close, relate to one another via a metric, scoring, probability, and the like, as described below. Machine-learning module, as described in further detail below, may generate a classifier using a classification algorithm, defined as a process whereby computing device and/or any module and/or component operating thereon derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a nociception parameter 112 training data classifier may classify elements of training data to elements that characterizes a sub-population, including subset of nociception biologic 108 such as gene expression patterns and epigenetic markers as it relates to a variety of degradation types and/or other analyzed items and/or phenomena for which a subset of training data may be selected.

Continuing in reference to FIG. 1, classifying nociception parameter 112 to nociception grouping 120 may include classifying the nociception parameter 112 to the nociception grouping 120 using the nociception classifier 124. Classification using nociception classifier 124 may include identifying which set of categories (nociception grouping 120) an observation (nociception parameter 112) belongs. Classification may include clustering based on pattern recognition, wherein the presence of nociception biologics 108, such as genetic indicators, symptoms, and the like, identified in nociception parameter 112 relate to a particular nociception grouping 120. Such classification methods may include binary classification, where the nociception parameter 112 is simply matched to each existing nociception grouping 120 and sorted into a category based on a "yes"/"no" match. Classification done in such a manner may include weighting, scoring, or otherwise assigning a numerical value to elements in nociception parameter 112 as it relates to each pain disorder type and assign a subject to a nociception grouping 120 that results in the highest score. Such a score may represent a "likelihood", probability, or other statistical evaluation that relates to the classification into nociception grouping 120.

Continuing in reference to FIG. 1, computing device 104 may assign the nociception grouping 120 as a function of the classifying. Classifying the nociception parameter 112 (input) to a nociception grouping 120 (output) may include assigning the nociception grouping 120 as a function of the nociception classifier 124 generated by the nociception classification machine-learning process. Training data for nociception classifier 124 may include sets of nociception parameters and/or nociception biologics 108, as described above, correlated to nociception grouping according to trends observed in the data for subsets of subjects. Subsets of subjects may include subjects belonging to a 'diagnosed cohort' that exhibits similar pain disorder characteristics. Such a set of training data may include nociception biologics 108 of the cohort, accounting for similar age, sex, and the like, as it relates to the subject experiencing pain. This way, classifier may be trained to relate nociception biologics 108 in the subject as it would classify the subject to the same (or different) nociception grouping. Such training data may be used to learn how to categorize a subject's nociception parameter 112 to nociception grouping(s) depending on trends in the data. In this way, nociception classifier 124 may also generate new nociception groupings depending on how well a subject may "fit" within a particular classification. For instance, if a particular pattern of subject data does not correlate well to categorizations observed from training data, classifier may have identified a novel grouping of pain disorder, manifestation of symptoms, and the like.

Continuing in reference to FIG. 1, classifying may include classifying the nociception parameter 112 to a nutrition-linked nociception disorder grouping. A "nutrition-linked nociception disorder grouping," as used in this disclosure, is a nociception disorder categorization that indicates a grouping which is sensitive to nutritional modification. Nutrition-linked nociception disorder grouping may include a category of current disorders that are not averse to nutritional modification, in that they may be addressed at least in part by varying nutrition levels in the subject. manipulation by varying nutritional consumption. A nutrition-linked nociception disorder grouping may include for instance and without limitation a disorder characterized by pain due to increased methylmalonic acid, indicative of a vitamin B12 deficiency, which may cause and/or exacerbate pain, where vitamin B12 supplementation may "cure" the deficiency where the disorder categorization may be changed with sufficient, sustained nutrient supplementation. Such classification may include identifying biomarkers or any nociception biologic 108 present in nociception parameter 112 which are resistant to nutritional changes and identifying which can be addressed with nutritional modification, altering dietary habits, nutrient supplementation, and the like.

Continuing in reference to FIG. 1, nutrition-linked nociception disorder grouping may include identifying relationships between nociception parameter 112 and nociception grouping which may have nutrition and/or nutrient metabolites as causative factors. In non-limiting illustrative examples, elevated pyroglutamate may be indicative of glutathione depletion, which may result in the manifestation of pain, among other accompanying symptoms. Glutathione depletion may be indicative of chronic protein deficiency in the diet, particularly essential amino acids, as well as increased oxidative stress. In further non-limiting illustrative examples, elevated xanthurenic acid may be indicative of vitamin B6 insufficiency, which can manifest as pain symptomology in subjects. Another non-limiting example may be found in elevated levels of acrolein metabolite 3-hydroxypropyl mercapturic acid, which may be found to be highly correlated with experiencing pain and/or discomfort. Nociception disorder groupings caused in-part by acrolein and/or its metabolites may not be immediately obvious and present difficulty to address. Acrolein is an unsaturated aldehyde found in cooked foods, particularly with oils (vegetable oil, and the like) which are cooked at or near their smoke point. Acrolein may also be a metabolite cause by glycerol in the metabolism of stored fats in individuals trying to lose weight. Such correlations are non-limiting examples that may be identified in training data of nociception biologics 108 as they may relate to symptoms that would classify a subject to a nutrition-linked nociception disorder grouping, which may be readily ameliorated, or even cured, with proper nutritional guidance.

Continuing in reference to FIG. 1, classifying may include classifying the nociception parameter 112 to a nutrition-linked pain disorder prevention grouping. A "nutrition-linked pain disorder prevention grouping," as used in this disclosure, is a nociception disorder categorization for which nutrients may act as a preventative measure. Nutrition-linked pain disorder prevention grouping may include a pain category which will occur, or is imminent, according to at least a nociception parameter 112 of the subject which may be prevented or ameliorated from nutritional modification. A nutrition-linked pain disorder prevention grouping may include a risk for developing pain from acrolein build-up in the future, where the risk may be reduced from nutritional intervention. Classification to such a category may include identifying biomarkers, or any nociception biologic 108, present in nociception parameter 112 which may be modified, over time, with sustained, chronic nutrient manipulation. In this way, nociception classifier 124 may identify groupings which are not imminent threats in healthy individuals but may represent sources of pain and/or discomfort in the future which may be avoided with nutritional guidance.

Continuing in reference to FIG. 1, computing device 104 is configured to identify, using the nociception grouping 120, a plurality of nutrition elements. A "nutrition element," as used in this disclosure, is an item that includes a nutrient intended to be used and/or consumed by subject for addressing nociception. A "nutrient," as used in this disclosure, is any biologically active compound whose consumption is intended for addressing and/or preventing nociception. Nutrition element 128 may include alimentary elements, such as meals (e.g. chicken parmesan with Greek salad and iced tea), food items (e.g. French fries), grocery items (e.g. broccoli), health supplements (e.g. whey protein), beverages (e.g. orange juice), and the like. Nutrition element 128 may be "personalized" in that nutrition elements are curated in a guided manner according to nociception parameter 112, nociception biologics 108, subject-designated symptoms, food allergies and/or intolerances, subject preferences, and the like. Nutrition element 128 may include supplementary use of oral digestive enzymes and/or probiotics which may also have merit as anti-pain nutritional measures. Nutrition elements 128 in a degradation prevention diet may include micronutrients such as vitamins, minerals, trace elements, electrolytes, such as selenium, folic acid, vitamin B12, vitamin D, bicarbonate, calcium, and the like. Nutrition elements may include phytonutrients and plant-based macromolecules such as chlorophyll, antioxidants such as the carotenoids (α-carotene, β-carotene, lycopene, lutein, cryptoxanthin), and the like. Nutrient elements 120 may contain biologically active compounds that are not typically considered as part of recommended daily nutrients, nor are they intended to provide appreciable amounts of calories, such as phytonutrients, nutraceuticals, antioxidants, and the like; for instance and without limitation, allium and bioactive ingredients present in cruciferous vegetables such as broccoli sprouts, which are known sources of antioxidants such as sulforaphane. Nutrition elements 128 may include a specific dietary category, such as a "ketogenic diet", "low glycemic index diet", "Paleo diet", among others.

Continuing in reference to FIG. 1, identifying the plurality of nutrition elements 128 includes generating a plurality of nutritional metrics associated with reduction of nociception as a function of the nociception grouping 120. A "nutritional metric," as used in this disclosure, is a quantification of a nutrient, and/or combination of nutrients, which hold significance to the classification of a subject to a nociception grouping 120; a nutritional metric may be associated with reduction of nociception where the nutritional metric represents a quantity of a nutrient and/or combination of nutrients consumption of which may result in a reduction of nociception. Nutritional metric 132 may include a minimal nutrient level, below which significant health concerns may exist. Nutritional metric 132 may include a current nutrient amount in the subject experiencing pain and/or discomfort, to which the subject is classified to a particular nociception grouping 120. Nutritional metric 132 may include a numerical value, or plurality of numerical values describing an average, median, standard deviation, variance, and the like, of a nutrient amount, or combination of nutrients as it relates to subjects of a particular nociception grouping 120. Nutritional metric 132 may include a plurality of numerical values describing a variety of mathematical evaluations of nutrient amounts in healthy individuals. Nutritional metric 132 may include a maximal acceptable nutrient level, above which may indicate health concerns. Nutritional metric 132 may include qualitative values such as binary values, Boolean values such as "true"/"false", "yes"/"no", and the like. Nutritional metric 132 may include quantitative values such as numerical values, mathematical expressions, formulas, equations, functions consisting of a plurality of numerical values according to a correlation or other mathematical relationship. In non-limiting exemplary embodiments, generating a plurality of nutritional metrics may include 1) a minimal acceptable nutrient amount for a subject, 2) a current nutrient amount in a subject, 3) a mean±SD for the nutrient in healthy subjects, and 4) a maximal nutrient amount appropriate for subject. In this way, a nutritional level may be established for the subject that may establish and maintain nutritional homeostasis for addressing pain and/or discomfort by keeping the subject above a custom minimal nutrient amount and below a custom maximal nutrient amount according to the current nutrient amount and how that current amount compares to an amount in a healthy cohort.

Continuing in reference to FIG. 1, identifying the plurality of nutrition elements 128 includes determining a respective effect of each nutritional metric of the plurality of nutritional metrics on the nociception parameter 112. A "respective effect," as used in this disclosure, is a change, consequence, and/or result in at least a nociception biologic 108, nociception parameter 112, nociception grouping 120, and/or amount of pain and/or discomfort in a subject achieved by consumption of a nutrient and/or combination of nutrients according to a nutritional metric. A respective effect 136 of a nutritional metric may be "no effect", "negligible effect", and/or "no calculated effect". Determining an effect of a nutritional metric may include determining how a nociception biologic 108 may change, such as an increase/decrease according to a particular amount of nutrient. For instance and without limitation, such a determination may include calculating the effect of chronic, sustained nutrient amounts in a diet for weeks and/or months on epigenetic factors, blood serum levels of nociception biologics 108, pain symptoms, and the like. Determining a respective effect 136 may allow determination of what is an acceptable minimal nutrient amount, maximal nutrient amount, the effect current nutrient levels is having on pain symptoms, among other respective effects 136 on nutritional metrics 132.

Continuing in reference to FIG. 1, determining a respective effect 136 of each nutritional metric 132 of the plurality of nutritional metrics 132 may include retrieving the respective effect 136 of each nutritional metric 132 on the nociception parameter 112 as a function of at least the nociception biologic 108. Computing device 104 may search for a nutrient effect using each nociception biologic 108, and/or combination thereof, to locate and retrieve effects correlated to nutrients targeting a nociception biologic 108. Retrieving an effect of a nutrient may include retrieving a hypothesis about the outcome for a subject after consuming a nutrient amount and/or amount of a combination of nutrients. Such a hypothesis may include an equation, function, among other mathematical forms, for instance derived from empirical relationships between a nutrient and the physiological integrity of an organ, biological system, experiencing pain, and the like. Retrieving an effect may include retrieving from a database, a research repository, or the like. Retrieving an effect may include, for instance, searching using the nociception biologic 108, a web browser, and the Internet, for a plurality of effects that nutrients may have to potentially identify a nutritional deficiency that may explain the pain symptom. Retrieving an effect may include searching using the nociception grouping 120 for an effect of a nutrient on the type of degradation. In some embodiments, retrieving an effect may include calculating at least an effect, for instance by deriving a function from training data using a machine-learning algorithm.

Continuing in reference to FIG. 1, in non-limiting illustrative examples, determining an effect of a nutrient may include calculating if a change in nociception grouping 120 may arise from adding and/or removing a nutrient from a subject's diet. For instance and without limitation, changing a nociception grouping 120 from "sustained chronic pain" to "intermittent acute pain" with increasing dietary vitamin B6, vitamin B12, plant-source protein, animal-source protein, reduction of acrolein by introducing nutrition elements 128 a subject may not currently consume, such as vegetable oils, tree nuts, seeds, green leafy vegetables, dairy products, and the like, while reducing cooked vegetables, cooked animal products (meats), and potentially adding particular supplements. Calculating an effect of a nutrient may include retrieving an empirical equation that describes relationships between a nutrient and nociception biologic 108, test results, nociception parameter 112, and the like. Calculating an effect of a nutrient may include deriving an algorithm, function, or the like, for instance using a machine-learning process and/or model. Calculating such an effect using machine-learning may include training data that includes a plurality of nutrients as it relates to effects on nociception groupings 124, nociception biologics 108, and the like.

Continuing in reference to FIG. 1, determining a respective effect of each nutrient amount of the plurality of nutrients may include generating a machine-learning model. Training data may include nutrient amounts correlated to their effect on the human body. For instance and without limitation, supplementation of amounts of fat-soluble vitamins, water-soluble vitamins, trace elements, minerals, electrolytes, among other nutrient categories in the diet may be correlated to renal function, liver function, vision integrity, bone mineral density, pain sensitivity, and the like. Such training data may originate from a database, research repository, clinical data, physician, plurality of subjects, or any other source described herein. Computing device 104 may generate a machine-learning model with such training data to derive an equation and/or function which describes relationships observed in the training data, for instance that a minimal amount of a vitamin is necessary, but that its effect is null if a second vitamin or mineral is not above a particular level. Computing device 104 may then automatedly derive a respective effect for each nutrient, wherein the effect may become increasingly defined by parameters relating to the type of pain in the subject. The effect may also be related to an equation wherein, the magnitude of effect may be determined for all amounts of the nutrient. In this way, a particular nutrient amount may be calculated based on the magnitude of effect desired.

Continuing in reference to FIG. 1, identifying a plurality of nutrition elements 128 includes calculating at least a nutritional level as a function of the respective effect 136 of each nutritional metric 132, wherein the at least a nutritional level includes an amount intended to address the nociception parameter. A "nutritional level," as used in this disclosure, is a therapeutic amount of a nutrient intended to address nociception parameter 112. Nutritional level 140 may include mass amounts of a vitamin, mineral, macronutrient (carbohydrate, protein, fat), a numerical value of calories, amounts of phytonutrients, antioxidants, probiotics, nutraceuticals, bioactive ingredients, and the like. Nutritional level 140 may include the calculated amount of a nutrient, or combination of nutrients, a subject should consume according to a plurality of nutritional metrics, such as the subject's current nutrient amount, the minimal and maximal acceptable amounts, and the nutrient amount in healthy individuals. Nutritional level 140 may include the amount the subject is intended to consume in a meal, a day, week, and the like. Nutritional level 140 may include the nutrient amount the subject is expected to have, for instance in the blood, after consuming a particular amount in the diet. In such an instance, nutritional level 140 may include an amount that is modified by a weighting factor that is determined according to a subject's pharmacokinetics. Such a weighting factor may include an empirical formula that weights each nutrient amount consumed according to the nutrient source (organic vs inorganic), the metabolism and absorption of the nutrient, the concentration that ends up in a tissue and/or fluid, and the like.

Continuing in reference to FIG. 1, calculating the nutritional level 140 may include generating a nutrition machine-learning model according to the training data, wherein training data includes a plurality of data entries correlating the respective effect of each nutritional metric to a plurality of nutritional level for each nociception grouping 102, and calculating the at least a nutritional level 140 as a function of the nutrition machine learning model and the plurality of nutritional metrics 132. Training data may include respective effect of each nutritional metric such as nutrient identities and amounts from [x, y], where x is a minimal acceptable nutrient amount and y is a maximal acceptable nutrient amount, and each discrete amount in the range of nutrient values is correlated to effects on nociception groupings 120, for instance vitamin A (retinol) correlated to glaucoma and pain and/or discomfort from optic nerve damage. Training data may include nutrient combinations from peer-reviewed studies correlated to pain management, for instance gamma linolenic acid, eicosatetraenoic acid, docosahexaenoic acid, omega-3 polyunsaturated fatty acids, glucosamine, chondroitin, and various salts of each in combination which may reduce joint pain in certain cohorts of subjects. In such an example, each nutrient may have a respective effect according to a plurality of nutritional metrics, wherein the values may be correlated to nutritional levels that should be sustained to address the nociception grouping 120 the subject belongs. Training data may include identified nutrient deficiencies in cohorts of subjects that may have particular pain and/or discomfort at higher than normal rates. Training data may correspondingly include nutrient surpluses, where overeating of particular nutrients may be correlated to pain and/or discomfort. Training data may originate from any source described herein, for instance and without limitation, from a physician, via subject input from a plurality of subjects, web browser and the Internet, a database, as described in further detail below, research repository, wearable device, physiological sensor, and the like.

Continuing in reference to FIG. 1, computing device 104 may calculate nutritional levels 140, for instance, by retrieving a default amount from a database. Computing device 104 may retrieve standard nutrient amounts, such as from a standard 2,000 calorie diet, and alter the amount according to a numerical scale associated with nociception biologics 108 in the nociception parameter 112. Such a calculation may include a mathematical expression using operations such as subtraction, addition, multiplication, and the like, for instance an equation that assigns a variable to the subject's body weight, level of pain described in the nociception parameter 112, and retrieves a start value of a vitamin and alters the amount using the mathematical expression. Alternatively or additionally, such a calculation may involve deriving a loss function, vector analysis, linear algebra, system of questions, among other mathematical heuristics, depending on the granularity of the process. Deriving such a process for calculating nutrient amounts may include machine-learning, as described above. Nutritional level 140 may include threshold values, or ranges of values, for instance and without limitation, between 80-120 mg vitamin C per 24 hours, wherein the range changes as a function of nociception parameter 112 and/or nociception grouping 120. Nutritional level 140 may be calculated as heat maps (or similar mathematical arrangements), for instance using banding, where each datum of nociception parameter 112 elicits a particular range of a particular nutritional level 140 or set of nutrient amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutritional levels 140, for instance in a database. The amounts may be re-calculated and converted according to a subject's nociception parameter 112. For instance, these amounts may relate to an average BMI, healthy adult male, for any range of calories, but may be adjusted according to unique subject-specific nociception biologics 108. In non-limiting illustrative examples, a geriatric woman who is on a 1,400 Calorie/day diet, with onset of osteoporosis, vision loss, and suffers advanced neuropathic pain may prompt calculation of nutritional levels 140 according to identified risk factors and the above nutritional levels 140 may be recalculated, where some amounts may increase, some may decrease, and some may remain constant.

Continuing in reference to FIG. 1, calculating nutritional levels 140 may include deriving a weighting factor to adjust, or otherwise re-calculate, an amount. Weighting factor may be determined by computing device 104, for instance, by querying for vitamin amounts according to data inputs identified in the nociception parameter 112. For instance in non-limiting illustrative examples, if nociception parameter 112 indicates the presence of elevated quinolinic acid, indicative of as a downstream metabolite of the kynurenine pathway, which metabolizes tryptophan. Increased levels of quinolinic acid may act as a neurotoxin, causing pain and/or discomfort in subjects. Respective effect 136 may be found in nutritional levels 140 relating to the slowing of quinolinic acid damage, specifically in supplementing the diet with kynurenic acid supplements, specific foods rich in antioxidants and phenols such as catechin hydrate, curcumin, epigallocatechin gallate, such as legumes, nuts, seaweed, avocados, cranberries, teas such as green tea, white tea, oolong tea, and the like, whereas it may be inversely associated with consumption of alcohol, certain animal products such as red meat and/or processed meat, and/or nicotine consumption. Although, vitamins found in such foods from organic sources may be superior from nonorganic sources, such as from commercially-available supplements, from a bioavailability standpoint. Additionally, per-subject pharmacokinetics, rates of metabolism and/or adsorption of nutrients may differ subject-to-subject, which may negate the effectiveness of proscribing particular diet types and nutritional levels 140 to subjects. In such an instance, computing device 104 may account for such details using machine-learning to derive more specific nutritional level 140 calculations and to more accurately calculate the amounts by which to increase/decrease nutrients. Therefore, computing device 104 may derive weighting factors to account for particular gene expression patterns, organic vs non-organic sources, pharmacokinetics, type of pain experience, and the like.

Continuing in reference to FIG. 1, in non-limiting illustrative examples, computing device 104 may use a machine-learning process to perform a machine-learning algorithm to derive per-subject pharmacokinetics, for instance of vitamin B6. Vitamin B6 deficiency may be indicative by elevated xanthurenic acid which may be observed in at least 1-in-6 subjects who experience chronic pain. The machine-learning algorithm may accept an input of numerical values including the total amount of protein consumed (in grams), total amount of vitamin B6 consumed (in mg) per day in a diet, and serum levels of the vitamin B6 vitamer, pyridoxal-5-phosphate, over the course of a month, and derive the rates of metabolism, or how 'well' the subject is obtaining the vitamin from nutrition elements 128 and adsorbing vitamin B6. In other words, the algorithm may derive a function such as using linear regression, vector quantization, least squares, among other algorithms, that describes the pharmacokinetics for that particular subject regarding what amount of vitamin B6 consumed, per amount of dietary protein, results in what corresponding amount of bioactive vitamin compound, as measured by the blood vitamer from a biological extraction. Such a function, derived from machine-learning, may then be used by computing device 104 with an input of the nociception parameter 112, which enumerates nociception biologics 108, to calculate an output which is a more accurate, customized, per-subject nutritional level 140 of vitamin B6, and potentially protein. Persons skilled in the art, upon benefit of this disclosure in its entirety, may appreciate that this process may be repeated for the full spectrum of nutrients, both required as part of a diet and not required as part of a diet, to control for specific metabolic differences in a population for addressing pain and/or discomfort.

Continuing in reference to FIG. 1, additionally, in non-limiting illustrative examples, computing device 104 may relate the concentrations of the metabolic products related to vitamins (e.g. vitamers), minerals, phytonutrients, probiotics, antioxidative compounds, biologically activity ingredients, prodrugs, and the like, to their effective concentrations in tissues related to various nociception groupings 120. For instance, computing device 104 may additionally search and retrieve data that relates the blood levels of the vitamin B6 vitamer, pyridoxal-5-phosphate, to the effective concentrations of vitamin B6 in the nervous system, which is particularly sensitive to aberrations in vitamin B6 for inducing pain symptomatology. Computing device 104 may store and/or retrieve values in a "look-up table", or graph a relationship as a mathematical function, among other ways of representing a data structure that relates the data identified in the search. Alternatively or additionally, computing device 104 may derive a function, for instance using machine-learning, which correlates the concentration of a compound in a particular biological extraction, such as blood, to varying amounts in tissues such as breast tissue, liver, CNS, and the like. This may prove helpful in calculating nutritional levels 140 as a function of subject consumption to specific target nutritional quantities within a particular organ/tissue according to the input data in the nociception parameter 112 for targeting pain originating from a particular tissue.

Continuing in reference to FIG. 1, computing device 104 is configured to identify the plurality of nutrition elements 128 as a function of the plurality of nutritional levels 140. Identifying the plurality of nutrition elements 128 may include retrieving nutrition elements that include at least a nutrient amount of the plurality of nutritional levels 140. Computing device 104 may accept an input of at least a nutritional level 140 and retrieve nutrition elements 128 by searching a database for nutrition elements according to the nutrient and the amount. Computing device 104 may accept an input of nutritional level 140 and may search using a web browser and the Internet for nutrition elements 128 according to the nutrient and its amount.

Continuing in reference to FIG. 1, identifying the plurality of nutrition elements 128 includes identifying the plurality of nutrition elements 128 as a function of the at least a nutritional level 140. Computing device 104 may identify the plurality of nutrition elements 128 by using nutritional level 140 as an input and generating combinations, lists, or other aggregates of nutrition elements 128 necessary to achieve nutrient amount 124. For instance, computing device 104 may use a template nutrient amount 124 of '200 mg vitamin C' and build a catalogue of nutrition elements 128 until the 200 mg vitamin C value is obtained. Computing device 104 may perform this task by querying for food items, for instance from a menu, grocery list, or the like, retrieving the vitamin C content, and subtracting the value from the nutrient amount 124. In non-limiting illustrative examples, computing device 104 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 104 may search according to a set of instructions such as food preferences, allergies, restrictions, and the like, provided by a physician, medical history, subject input, among other sources, and subtract each identified nutrition element 128 nutrient from nutrient amount 124 until a combination of nutrition elements 128 that represents a solution is found. Once a solution is found, computing device 104 may generate a file of nutrition elements 128 and store in a database, as described in further detail below. In this way, computing device 104 may generate customized meals, health shakes, recipes, and the like.

Continuing in reference to FIG. 1, identifying the plurality of nutrition elements 128 may include retrieving the nutrition elements 128 as a function of the nociception grouping 120. Identifying nutrition element 128 according to nociception grouping 120 may include querying, for instance using a web browser and the Internet, for foods, supplements, bioactive ingredients, and the like, which are correlated with a particular nociception grouping 120. For instance and without limitation, computing device 104 may organize a search for foods intended for "arthritis pain", wherein an entire diet may be crafted around target nutritional levels 140 and the categorization of the nociception parameter 112 to "arthritic pain". In such an example, the nutrition elements 128 are outputs generated from an input search criteria of "arthritic pain". The output elements become "personalized" as they are arranged into daily, weekly, monthly, and the like, individual meals and/or meal schedule according to a subject's particular calculated nutritional levels 140. The nociception grouping 120 may serve as a filtering step, wherein a search is guided by the nociception parameter 112 as it was classified to a nociception grouping 120 where particular nutritional elements may be included and/or avoided (for instance if they exacerbate symptoms).

Continuing in reference to FIG. 1, computing device 104 is configured to generate a nociception nourishment program using the plurality of nutrition elements 128. A "nociception nourishment program," as used in this disclosure, is a collection of at least a nutritional level 140 and at least a nutrition element 128 for addressing pain and/or discomfort. Nociception nourishment program 144 may be organized into a frequency and/or magnitude. A "frequency," as used in this disclosure, is a number of consumption occurrences associated with a time course, such as daily, weekly, monthly, and the like, of which a nutrition element 128 is intended to be consumed. Frequency may be determined as a function of the respective effect 136, wherein the frequency of consumption is tailored to provide a sufficient minimal nutrient level over a time. A "magnitude," as used in this disclosure, is a serving size of at least a nutrition element 128 as a function of the respective effect 136. Identifying the magnitude associated with a nutrition element 128 may include calculating a serving size of the at least a nutrition element 128 as a function of the respective effect 136. Nociception nourishment program 144 may include gathering, classifying, or otherwise categorizing nutritional level 140 and/or nutrition element 128 lists, which incorporates nociception grouping 120-specific recommendations. For instance, nutrition elements 128 may be scored with a numerical score scale that associates a meal, beverage, supplement, and the like, with preventing pain symptoms, ameliorating to pain symptoms, and the like. Nociception nourishment program 144 may include selecting nutrition elements 128 according to a threshold score, where items above the threshold are selected and arranged into meals. Threshold score may include a daily threshold, wherein nutrition elements 128 are selected each day according to the threshold; and threshold may include a numerical value relating to symptom prevention, a calculated nutritional level 140, among other outputs of system 100 described herein. Determining nociception nourishment program 144 may include machine-learning. For instance and without limitation, training a machine-learning model to identify a scoring rubric for building the nociception nourishment program 144 based on some criteria such as preventing future pain, alleviating symptoms, decreasing and/or increasing concentration of nociception biologic 108, among other criteria. Nociception nourishment program 144 may relate specific nociception grouping 120 to specific nutrients of interest and provide nutrition element 128 scheduling times and serving sizes for each meal. Nociception nourishment program 144 may differ from one subject to the next according to the magnitude of the disease outline (nociception grouping 120 and nociception parameter 112).

Continuing in reference to FIG. 1, generating the nociception nourishment program 144 may include receiving a subject preference. A "subject preference," as used in this disclosure, is a subject input that designates a preference related to at least a nutrition element 128. Subject preference may include designations of nutrition elements 128 to avoid and/or include such as particular food groups, condiments, spices, dietary restrictions such as 'no animal products', cuisine type such as 'Mediterranean foods', time of day for eating such as 'fasting before 10 am', and the like. Subject preference may include indications of allergies, food intolerances, and the like, which may represent constraints on curating nutrition elements 128. In this way, computing device 104 may accept an input of subject preference filter, sort, classify, or otherwise modify the data structure of nutrition elements 128 and schedule the nutrition elements 128 into nociception nourishment program 144 in a custom, per-subject manner. Computing device 104 may modify the plurality of nutrition elements 128 as a function of the subject preference, for instance by providing recipes with steps omitted, new steps added, or entirely new recipes altogether utilizing the same or different nutrition elements 128. Computing device 104 may modify the plurality of nutrition elements 128 as a function of the subject preference by generating a new file, based on the preference, and storing and/or retrieving the file from a database, as described in further detail below.

Continuing in reference to FIG. 1, generating the nociception nourishment program 144 may include generating a linear programming function with the at least the plurality of nutrition elements 128 wherein the linear programming function outputs at least an ordering of a plurality of nutrition elements 128 according to constraints from the nociception grouping 120 and the nutritional level 140. Generating the nociception nourishment program 144 may include generating a linear programming function with the at least a plurality of nutrition elements 128 wherein the linear programming function outputs at least an ordering of a plurality of nutrition elements 128 according to constraints from the subject preference. A "linear programming function," as used in this disclosure, is a mathematical function that may be used by computing device 104 to score each possible combination of nutrition elements 128, wherein the objective function may refer to any mathematical optimization (mathematical programming) to select the 'best' element from a set of available alternatives. Selecting the 'best' element from a set of available alternatives may include a combination of nutrition elements 128 which achieves the nutritional level(s) 140 in addressing nociception parameter 112 and/or nociception grouping 120 in a subject. Linear programming function may be simply referred to as "objective function".

Continuing in reference to FIG. 1, an objective function may include performing a greedy algorithm process. A "greedy algorithm" is defined as an algorithm that selects locally optimal choices, which may or may not generate a globally optimal solution. For instance, computing device 104 may select combinations of nutrition elements 128 so that values associated therewith are the best value for each category. For instance, in non-limiting illustrative example, optimization may determine the combination of the most efficacious 'frequency, 'magnitude', 'probiotic product', 'vegetable containing a polyphenol', 'nutrient amount per meal', 'fruit containing an antioxidant', among other categories to provide a combination that may include several locally optimal solutions but may or may not be globally optimal in combination.

Still referring to FIG. 1, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a subject, as indicated by subject preference, and a linear program may use a linear objective function to calculate combinations, considering how these limitations effect combinations. In various embodiments, system 100 may determine a set of instructions towards addressing a subject's nociception grouping 120 that maximizes a total pain prevention score subject to a constraint that there are other competing objectives. For instance, if achieving one nutrient amount by selecting from a first nutrition element 128 category may result in needing to select a second nutrition element 128 from a second category, wherein each may compete in degradation prevention (e.g. adopting two or more diet types simultaneously may not be feasible, a vegan option and a non-vegan option, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression of an output of which a process minimizes to generate an optimal result. For instance, achieving nutritional levels 140 may be set to a nominal value, such as '100', wherein the objective function selects elements in combination that reduce the value to '0', wherein the nutritional levels 140 are '100% achieved'. In such an example, 'maximizing' the optimal result would be selecting the combination of nutrition elements 128 that results in achieving nutritional levels 140 by minimizing the difference. As a non-limiting example, computing device 104 may assign variables relating to a set of parameters, which may correspond to pain symptom prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, generating the nociception nourishment program 144 may include generating a nociception program classifier using a nociception program classification machine-learning process to classify nutrition elements 128 to the plurality of nutritional levels 140, and outputting the plurality of nutrition elements 128 as a function of the nociception program classifier. Nociception program classifier may include any classifier, as described above, generated by a classification machine-learning process using training data, performed by a machine-learning module as described in further detail below. Training data for nociception program classifier may include sets of data entries that include nutrition elements 128 that are correlated to nutritional levels 140 that classifier may be trained to automatedly locate, sort, and output nutrition elements 128 according to calculated nutritional levels 140 for the subject. Such training data may originate via a database, the Internet, research repository, and the like, as described above for training data for other machine-learning processes. Training data may include nutrition elements 128, correlated to nutrition facts, nutrients, medicinal qualities, and the like, which a classifier may be trained to locate relationships that aid in locating nutrition elements 128 specifically for addressing nociception grouping 120. Nociception program classifier may accept an input of nutritional levels 140 and output a plurality of nutrition elements 128 with associated frequency and magnitude schedule according to relationships between nutrition elements 128 and nutritional levels 140. For instance and without limitation, nociception program classifier may identify relationships between individual fruits and vegetables, that when more vegetables are selected, certain fruits may not be necessary to schedule within the same timeframe. Such a classification process may determine a function, system of equations, and the like, which can be solved for in determining which nutrition elements 128 are useful toward obtaining the nutritional levels 140, while not missing some lower limits of nutritional levels 140 (trace elements) and not exceeding upper limits for other nutritional levels 140 (calories).

Continuing in reference to FIG. 1, nociception nourishment program may include a nociception nourishment index. A "nociception nourishment index," as used in this disclosure, is a score that reflects the subject's pain management as a function of what the subject has consumed. Nociception nourishment index 148 may reflect the level of subject participation in the nociception nourishment program 144 and the level of pain in the subject as a function of adherence to nociception nourishment program 144. Nociception nourishment index may include a numerical value, metric, parameter, and the like, described by a function, vector, matrix, or any other mathematical arrangement. Nociception nourishment index 148 may include enumerating a subject's current nourishment as it relates to managing pain symptomology, nociception biologics 108, and/or pain prevention.

Continuing in reference to FIG. 1, generating the nociception nourishment program 144 nociception nourishment index 148 may include receiving nutritional input from a subject interaction with a client device. "Nutritional input," as used in this disclosure, is an amount of a nutrient consumed by a subject. Nutritional input may be received and/or calculated, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. Computing device 104 may receive nutritional input from a subject. Nutritional input, for instance and without limitation, may include food items that have associated nutrition facts, wherein computing device 104 may calculate, weight, or otherwise modify, the nutritional input from the subject, such as with a weighting factor. This results in accurate, per-subject nutritional input, where each nutrition element 128 consumed may be broken down into its constituent nutrients and what amount of that nutrient was absorbed by the subject. That nutritional input may be used to determine the amount of target nutritional levels 140 summarized in the nociception nourishment program 144 the subject is consuming. Adherence to nociception nourishment program 144 may be determined from nutritional input, and the pain level may be determined from the adherence to the nociception nourishment program 144. Nutritional input of a subject may include a designation of any nutrition elements 128 subject may have consumed, such as via the client device and graphical user interface. Nutrition elements 128 may have nutritional levels 140 associated therewith, which may be applied to a subject's current nociception parameter 112, nociception grouping 120, and the like, representing an update to the data as the subject consumes nutrition elements 128. Applying the nutritional levels 140 may include calculating a difference in nociception nourishment index 148. Applying the nutritional levels 140 may include calculating a change in pain disorder risk, pain levels, and/or incidence of symptoms in the future, as a function of achieving nutritional levels 140.

Continuing in reference to FIG. 1, generating nociception nourishment index 148 may include generating an indexing model using training data including a plurality of data entries correlating the respective effect of each nutrition element in the nociception nourishment program on the nociception parameter. An "indexing model", as used in this disclosure, is a machine-learning model that derives a scoring function for assigning nociception nourishment index 148 according to nutritional input. Indexing model 152 may include any machine-learning algorithm, model, and/or process, described herein, that may be performed by machine-learning module as described in further detail below. Training data for indexing model 152 may originate from a database, retrieved by a web browser and the Internet, received as input via a client device, a plurality of subjects, a physician, peer-reviewed research repository, among any other source described herein. Training data for indexing model 152 may include respective effects 136 of nutrition levels 140 correlated to effects on nociception biologic 108 and/or nociception parameter 112, so that relationships observed in such training data may be used to derive a mathematical relationship, such as a function, to determine a scoring function for how each consumed nutrition element relates to achieving some amount of nutrition level 140, which is tied to a respective effect on nociception parameter 112. Indexing model may then use such training data to determine the scoring index, the maximal score, minimal score, and the incrementation by which in increase/decrease score according to what subject consumes—both from nociception nourishment program 144 and items from outside the program.

Continuing in reference to FIG. 1, alternatively or additionally, nociception machine-learning model 116 may be used to derive numerical scales for providing numerical values to nociception parameter 112. Nociception machine-learning model 116 may "learn" the upper and lower limits to the numerical scale, the increments to providing scoring, and the criteria for increasing and decreasing elements encompassed in the nociception parameter 112. Such a scoring function may operate similarly to the indexing model 152 for providing the nourishment index 148. In doing so, nociception machine-learning model 116 may derive a theoretical scale for providing an objective value to pain and/or discomfort experienced by the subject (nociception parameter 112), wherein the nociception parameter 112 may change as a function of the nourishment index 148 of the subject.

Continuing in reference to FIG. 1, computing device 104 may use indexing model 152 to derive a numerical scale along which to provide a numerical value to nociception nourishment index 148. For instance, such a machine-learning model may be trained with training data, wherein training data contains data entries of nutritional levels 140 correlated to pain symptom prevention. Such a machine-learning model may be trained with said training data to be used by computing device 104 to correlate the consumption of particular foods in nociception nourishment program 144 to achieving some level of nutritional level 140, and how the nutritional level 140 relates to body symptom alleviation, pain level, nociception grouping 120, and/or nociception parameter 112. Training data for generating nociception nourishment index 148 may include a plurality of data entries including nutrient amounts correlated to effects on pain, wherein the indexing model 152 may accept inputs of nutrition elements a subject has consumed and automatedly determine how the score should increase and/or decrease based on the nutritional level 140 targets for the subject.

Continuing in reference to FIG. 1, in non-limiting illustrating examples, falling short of glutamate and B vitamin nutritional levels 140, may have a particular effect on nociception nourishment index 148 for an individual who has been classified to a certain nociception grouping 120. Where, chronically falling short of the nutritional level 140 results in a (−3) score each month but falling within the nutritional level 140 range for those two nutrients affords (+1) score for each 8 month; the target amount for the preceding month may dictate the score change for each subsequent month. In such a case, a machine-learning model may derive an algorithm which dictates the amount to increase/decrease nociception nourishment index 148 for that particular nociception grouping 120 according to the nutritional levels 140. In this case, the indexing model 152 may be trained to identify the relationship between nutritional levels 140 and effect on pain reduction to derive an equation that relates scoring criteria to what is consumed. The score is then calculated using the indexing model 152 and nutritional input. Consumption by the subject may include amounts and identities of nutrition elements 128. In this way, computing device 104 may calculate a nociception nourishment index 148 as a function of a subject's participation in nociception nourishment program 144, where nociception nourishment index 148 is updated with each nutrition element 128 consumed by subject.

Figure 2:
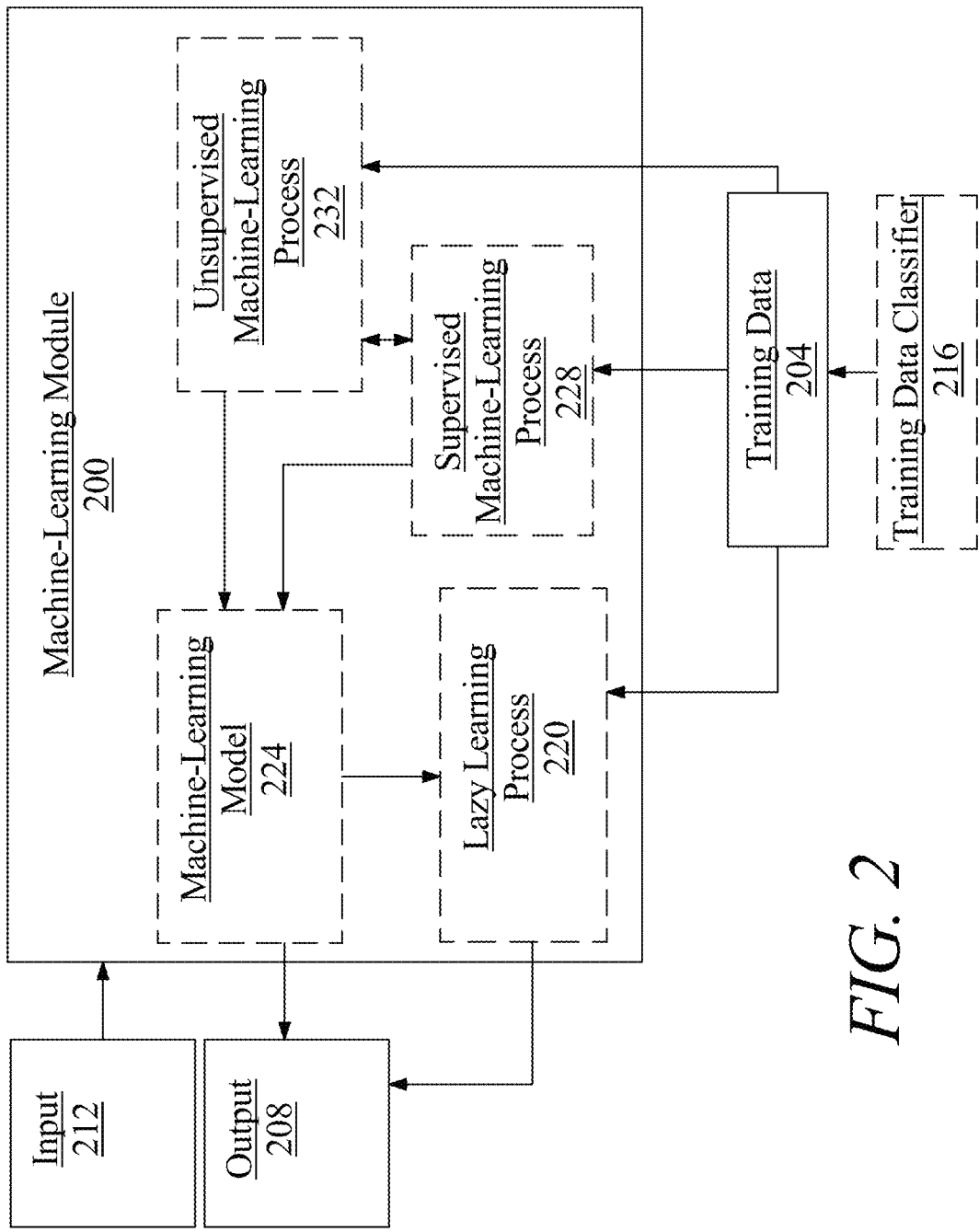
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of nociception biologics 108 (such as neurotransmitter metabolites and pain symptoms as it relates to nociception parameter 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying nociception biologic 108 elements to nociception parameter 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to nociception parameter 112 and/or nociception nourishment index 148, and the like, as described above, to "learn" the upper and lower limits to the numerical scale, the increments to providing scoring, and the criteria for increasing and decreasing elements encompassed in the nociception parameter 112 and/or nociception nourishment index 148, and the like. A machine-learning model may be used to "learn" which elements of nociception biologics 108 have what effect on nociception parameter 112, and which elements of nociception parameter 112 are affected by particular nutrition elements 128 and the magnitude of effect, and the like. The magnitude of the effect may be enumerated and provided as part of system 100, where nutrition elements 128 are communicated to subject for their degradation reduction properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a nociception parameter 112 (potentially classified into nociception groupings 120), as described above as inputs, nutrition element 128 outputs, and a ranking function representing a desired form of relationship to be detected between inputs and outputs; ranking function may, for instance, seek to maximize the probability that a given input (such as nutritional levels 140) and/or combination of inputs is associated with a given output (nociception nourishment program 144 that incorporate nutrient elements 120 to achieve nutritional levels 140 that are 'best' for nociception grouping 120) to minimize the probability that a given input is not associated with a given output, for instance finding the most suitable times to consume meals, and what the meals should be, and the like. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon the benefit of reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
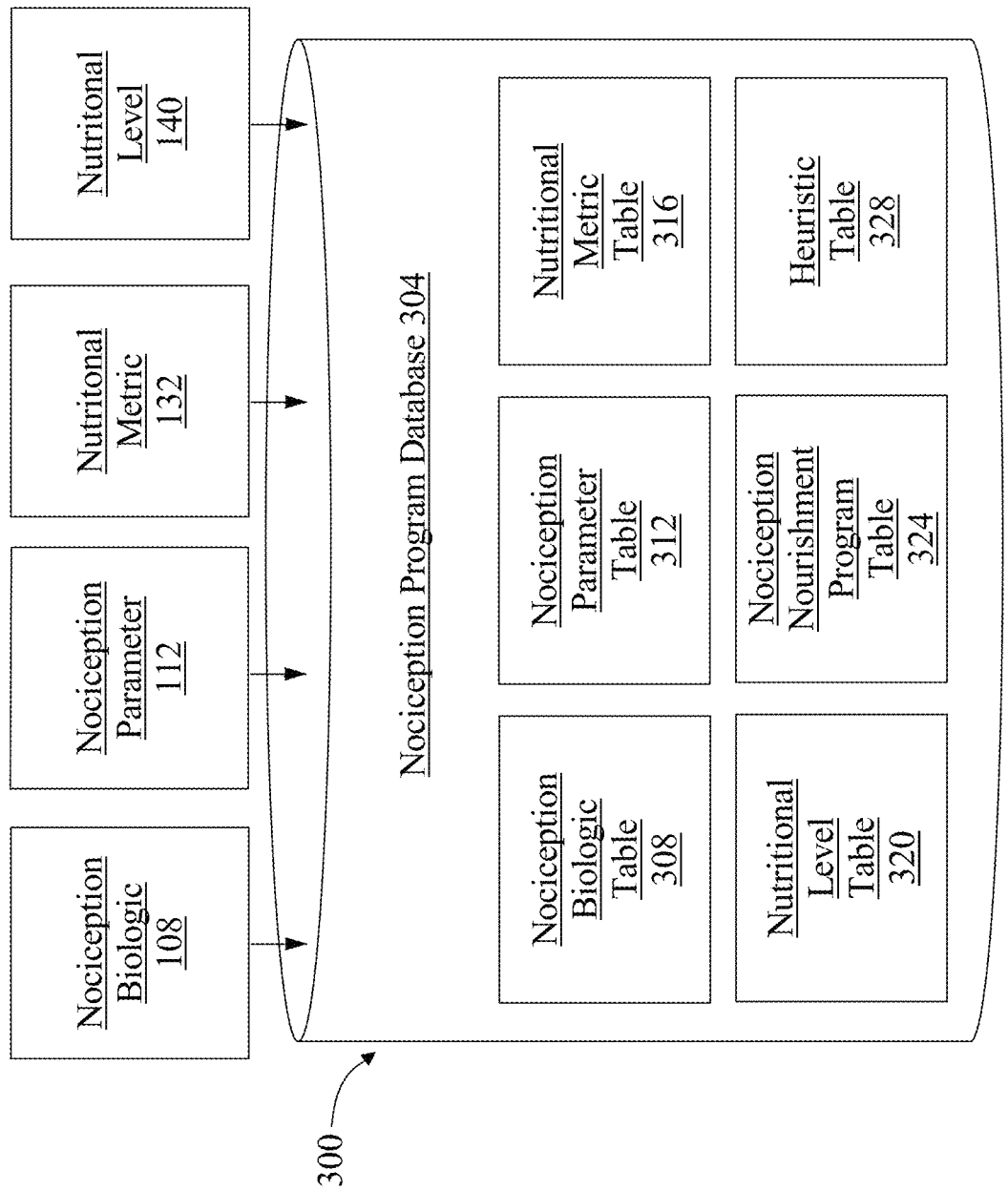
FIG. 3 is a block diagram of a nociception program database.

Referring now to FIG. 3, a non-limiting exemplary embodiment 300 of a nociception program database 304 is illustrated. Nociception biologic(s) 108 from a plurality of subjects, for instance for generating a training data classifier 216, may be stored and/or retrieved in nociception program database 304. Nociception biologic(s) 108 data from a plurality of subjects for generating training data 204 may also be stored and/or retrieved from a nociception program database 304. Computing device 104 may receive, store, and/or retrieve training data 204, wearable device data, physiological sensor data, biological extraction data, and the like, from nociception program database 304. Computing device 104 may store and/or retrieve nociception machine-learning model 116, nociception classifier 124, among other determinations, I/O data, models, and the like, from nociception program database 304.

Continuing in reference to FIG. 3, nociception program database 304 may be implemented, without limitation, as a relational database, a key-value retrieval database such as a NOSQL database, or any other format or structure for use as a database that a person skilled in the art would recognize as suitable upon review of the entirety of this disclosure. Nociception program database 304 may alternatively or additionally be implemented using a distributed data storage protocol and/or data structure, such as a distributed hash table and the like. Nociception program database 304 may include a plurality of data entries and/or records, as described above. Data entries in a nociception program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, nociception program database 304 may include, without limitation, nociception biologic table 308, nociception parameter table 312, nutritional metric table 316, nutritional level table 316, nociception nourishment program table 324, and/or heuristic table 328. Determinations by a machine-learning process, machine-learning model, ranking function, and/or classifier, may also be stored and/or retrieved from the nociception program database 304. As a non-limiting example, nociception program database 304 may organize data according to one or more instruction tables. One or more nociception program database 304 tables may be linked to one another by, for instance in a non-limiting example, common column values. For instance, a common column between two tables of nociception program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a nociception program database 304 may include, as a non-limiting example, a nociception biologic table 308, which may include categorized identifying data, as described above, including nociception biologic 108 data such as genetic data, epigenetic data, microbiome data, physiological data, biological extraction data, neurotransmitter metabolite types and concentrations, current nutritional deficiencies, physician assessments, pain assessment data, and the like. Nociception biologic table 308 may include nociception biologic 108 categories according to gene expression patterns, SNPs, mutations, enzyme specific activity and concentration, phosphorylation data, proteasomal degradation data, data concerning metabolism of nutrition elements 128, pharmacokinetics, nutrient absorption, and the like. One or more tables may include nociception parameter table 312, which may include data regarding nociception biologic 108, thresholds, scores, metrics, values, categorizations, and the like, that system 100 may use to calculate, derive, filter, retrieve and/or store linked tables to, for instance and without limitation, mathematical expressions that describe the impact of each nociception biologic 108 datum on nociception parameter 112, for instance threshold values for gene expression, and the like, as it relates to nociception parameters, pain levels, nociception grouping 120, and the like. One or more tables may include nutritional metric table 316, which may include data on current levels of nutrition in subject, maximal nutrient thresholds, minimal nutrient thresholds, nutrients averages and statistical evaluations among cohorts of subjects, data from alike subjects with similar nociception biologic 108, nociception parameter 112, and the like, that system 100 may use to calculate, derive, filter, retrieve and/or store respective effects 136 between nociception parameters 112 and nutritional metrics 132. One or more tables may include nutritional level table 316, which may include functions, model, equations, algorithms, and the like, using to calculate or derive nutritional levels 140 relating to nociception parameter 112 and/or nociception grouping 120, may include nutritional levels 140 organized by nutrient, nutrient classification, age of subject, sex, pain severity, and the like, which may be used to calculate, filter, or otherwise determine therapeutic amounts of nutrients. One of more tables may include a nociception nourishment program table 324, which may include nutrition element 128 identifiers, frequencies, magnitudes, consumption models associated with scheduling nutrition elements 128 regarding times to eat, identifiers of meals, recipes, ingredients, diet types, and the like. One or more tables may include, without limitation, a heuristic table 328, which may organize rankings, scores such as nociception nourishment indexes 148, models such as indexing model 152 and other scoring functions, inputs and outputs such as nutritional input and weighting factors, functions, numerical values, scales, arrays, matrices, and the like, that represent determinations, probabilities, metrics, parameters, values, and the like, include one or more inputs describing potential mathematical relationships, as described herein.

Figure 4A:
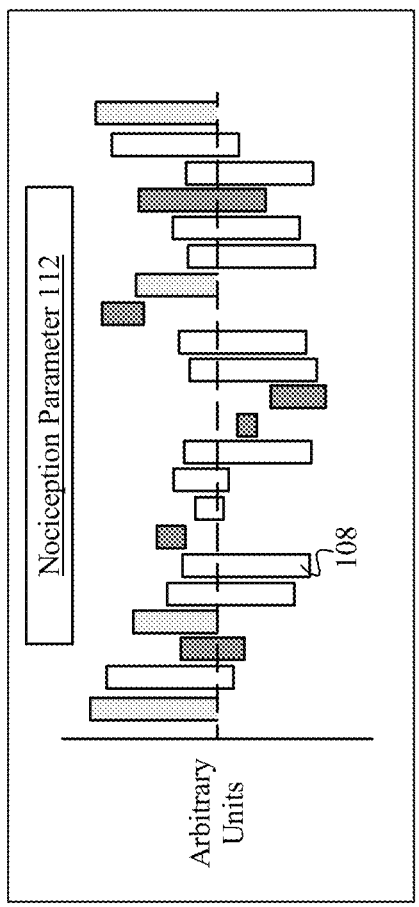
FIGS. 4A-B are diagrammatic representations of an exemplary embodiment of a nociception parameter.
Figure 4B:
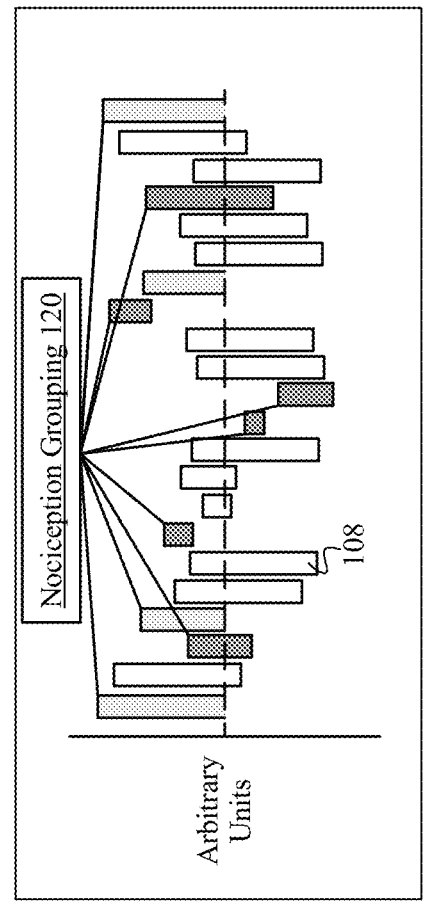

Referring now to FIG. 4A, a non-limiting exemplary embodiment 400 of a nociception parameter 112 is illustrated. Nociception parameter 112 may include a variety of nociception biologic 108 categories, for instance 22 distinct categories, as shown in FIGS. 4A and 4B. Each nociception biologic 108 may be assigned a value, such as an arbitrary value, where some nociception biologics 108, such as those shaded in light grey, may relate to absolute scales from [0, x], where x is a maximal value and the range of values for the nociception biologic 108 cannot be below a 'zero amount'. Some nociception biologics 108, such as those shaded in dark grey, may relate to gene expression levels, wherein, the nociception biologic 108 is enumerated as a 'box plot' that illustrates the range of expression in a population of subjects organized according to, for instance tissue type. In such an example, the dashed line may relate to a 'normal threshold' above which is elevated gene expression, below which is decreased expression level. Each nociception biologic 108 may have associated with it a numerical score, or some other identifying mathematical value that computing device 104 may assign. Persons skilled in the art, upon the benefit of this disclosure in its entirety, may appreciate that for each subject, any number of nociception biologics 108 may be enumerated and assigned a value according to nociception machine-learning model 116. Nociception parameter 112 may be graphed, or otherwise displayed, according to the enumeration by nociception machine-learning model 116. Each bar of the bar graph, or combinations of bar graph categories, may instruct classification of a subject's nociception parameter 112 to a nociception grouping 120.

Referring now to FIG. 4B, in non-limiting exemplary illustrations nociception parameter 112 may be classified to a nociception grouping 120. Some and/or all of the nociception biologics 108 summarized in nociception parameter 112 may be used to classify an individual to a particular nociception grouping 120. For instance, as shown in FIG. 4B, ten of the 22 nociception biologic 108 categories may be used to classify nociception parameter 112 to one or more nociception groupings 124. Alternatively or additionally, nociception machine-learning model 116 may be trained to assign nociception biologic 108 to a nociception grouping 120, wherein computing device 104 may derive the identity of nociception grouping 120 according to which nociception grouping 120 has the most identifying data points. Alternatively or additionally, nociception classifier 124 may be trained to assign subject to a nociception grouping 120 according to patterns observed in nociception biologics 108, for instance according to data from a subset of subjects.

Figure 5:
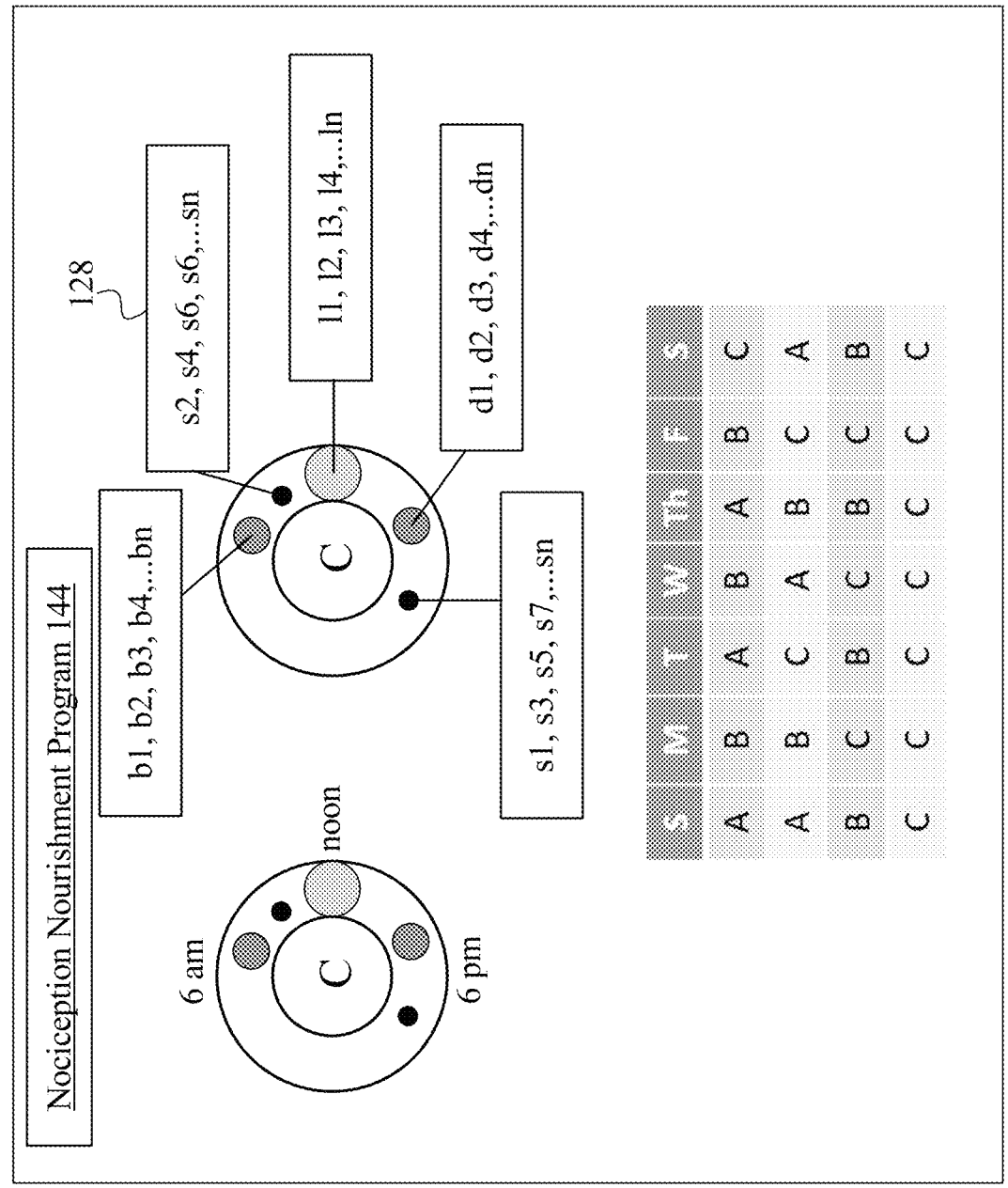
FIG. 5 is a diagrammatic representation of a nociception nourishment program.

Referring now to FIG. 5, a non-limiting exemplary embodiment 500 of a nociception nourishment program 144 is illustrated. Nociception nourishment program 144 may include a schedule for arranging nutrition elements 128, according to for instance a 24-hour timetable, as designated on the left, where consumption is planned along a subject's typical day-night cycle, beginning at ~6 am until just after 6 pm. In this way, the importance of providing regularly scheduled meal times may help provide normalcy to the subject's circadian rhythm, which may provide some alleviation for pain and/or discomfort, especially in maintaining tightly regulated nutritional levels 140. Nutrition element 128 may include breakfast (denoted as mid-sized dark grey circle), which may correspond to a file of breakfast-related plurality of nutrition elements 128 (denoted b1, b2, b3, b4 . . . bn, to the nth breakfast item). Nutrition element 128 may include snacks eaten throughout the day to, for instance achieve nutritional levels 140 missing from meals (denoted as small black circles), which may correspond to a file of snacking-related plurality of nutrition elements 128 (denoted s1, s2, s3, s4 . . . sn, to the nth snacking item). Nutrition element 128 may include dinner (denoted as large-sized light grey circle), which may correspond to a file of dinner-related plurality of nutrition elements 128 (denoted d1, d2, d3, d4 . . . dn, to the nth dinner item). Nociception nourishment program 144 may include a variety of diets, as denoted in the monthly schedule at the bottom, Sunday through Saturday. Nociception nourishment program 144 'C' is shown, which may be an idealistic goal for subject to achieve by the end of the month, where nourishment plan 'A' and 'B' are intermediate plans intended to wean subject to the 'ideal' plan. Nutrition elements 128 classified by 'meal type' may be further modified by 'A' and 'B' according to subject preferences 148 collected by computing device 104 throughout the process. Circle sizes, denoting nutrition element 128 classes may relate to magnitude, which are graphed along the circle corresponding to the frequency they are expected to be consumed. Subject may indicate which nutrition element 128 from each category was consumed, and when it was consumed, as inputs to calculate at nociception nourishment index 148 according to an indexing model 152.

Figure 6:
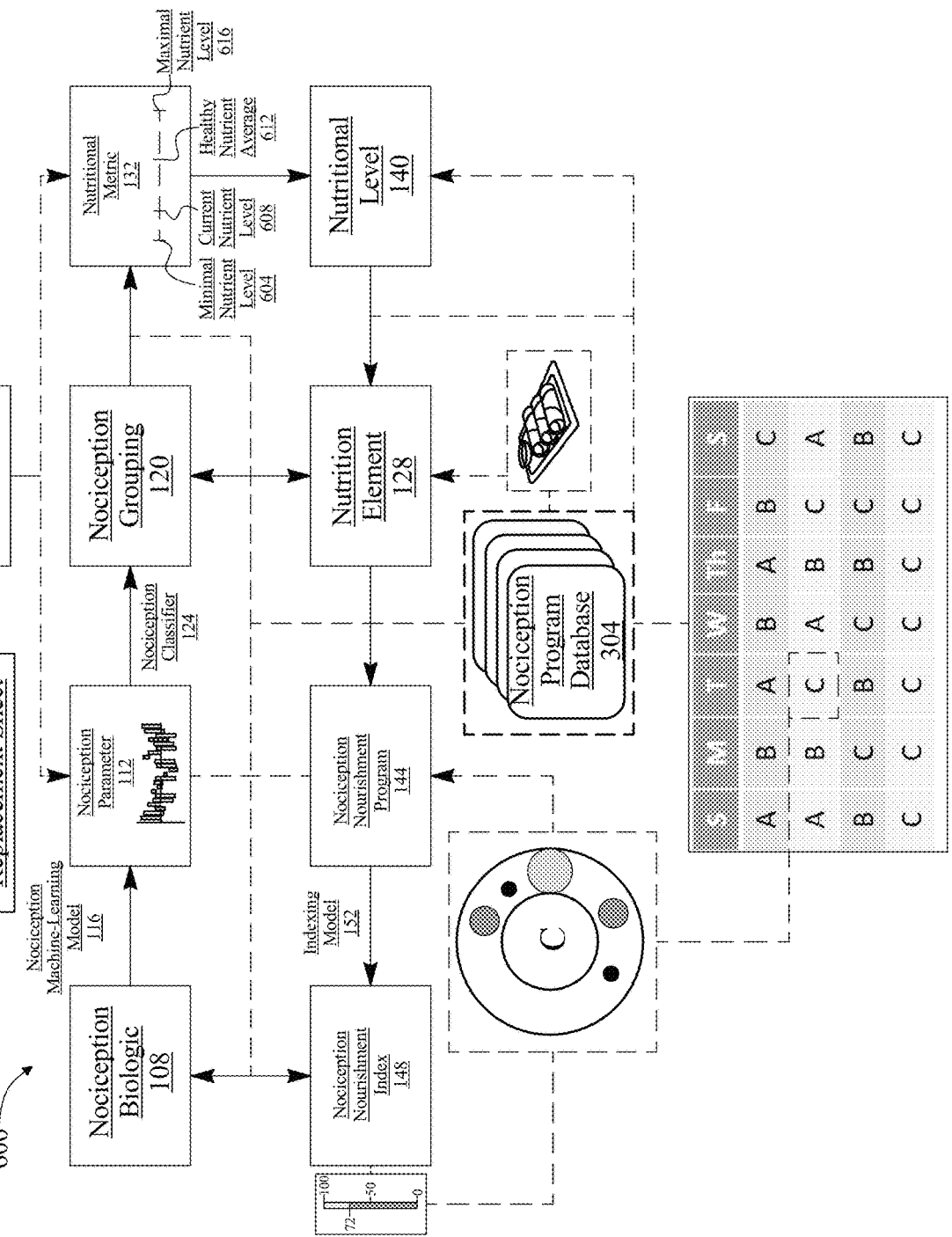
FIG. 6 is a diagrammatic representation of an overview of a nociception nourishment program.

Referring now to FIG. 6, a non-limiting exemplary embodiment 600 of an overview of generating a nociception nourishment program 144 is illustrated. Computing device 104 may receive nociception biologic(s) 108 and generate nociception machine-learning model 116 to derive equations and/or scoring functions from training data to output nociception parameter(s) 112. Computing device 104 may generate a nociception classifier 124 to automatically classify a subject's nociception parameter(s) 112 to a nociception grouping 120, such as a determination about the type of pain experienced, pain disorder, among other classifications. Classification may include identifying a nutrition-linked pain disorder category, which may uncover an etiology for pain in the subject that is indicative of a nutritional deficiency, surplus, or some other inconsistency in nutrition from what is considered 'healthy'. Computing device 104 may then determine a plurality of nutritional metrics 132, for instance and without limitation, which relate to minimal nutrient level 604, current nutrient level 608, healthy nutrient average 612, and/or maximal nutrient level 616. Such nutritional metrics may be used as inputs with nociception parameter(s) 112 to generate an output of a respective effect 136, which may include a relationship between the current nutrient level and the amount of pain a subject experiences. Nutritional metric(s) 132 may be used as inputs for computing device 104 to output nutritional level 140, which may include a therapeutic amount of a nutrient and/or nutrient combination intended to address pain and/or discomfort.

Still referring to FIG. 6, nutritional level 140 may be stored and/or retrieved from a database, such as nociception program database 304, as described herein. Computing device 104 may use nutritional level 140 as an input to determine nutrition element(s) 128. Nutrition elements 128 may be stored and/or retrieved from nociception program database 304. Computing device may accept a nutrition elements 128 as inputs, along with constraints imposed from subject preferences, frequency and magnitude associated with maintain minimal and/or maximal acceptable nutritional metrics 132, to generate an objective functions, such as a linear programming function, which can output at least an ordering of the plurality of nutrition elements 128 according to the constraints Orderings of plurality of nutrition elements 128 may be stored and/or retrieved from nociception program database 304. Computing device 104 may then, using the plurality of nutrition elements 128, generate a nociception nourishment program 144. Nociception nourishment program 144 may include nutritional elements 128 thoughtfully curated according to daily schedules, including magnitudes, frequencies, and food ordering information, including recipes if meals with be made by subject. Computing device 104 may provide a nociception nourishment index 148 by generating an indexing model 152 for providing the subject a scoring criteria and a numerical assessment of pain management. Such a nociception nourishment index 148 may increase with adherence and participation in nociception nourishment program 144, including providing new up-to-date nociception biologic 108 data and providing nutritional input.

Figure 7:
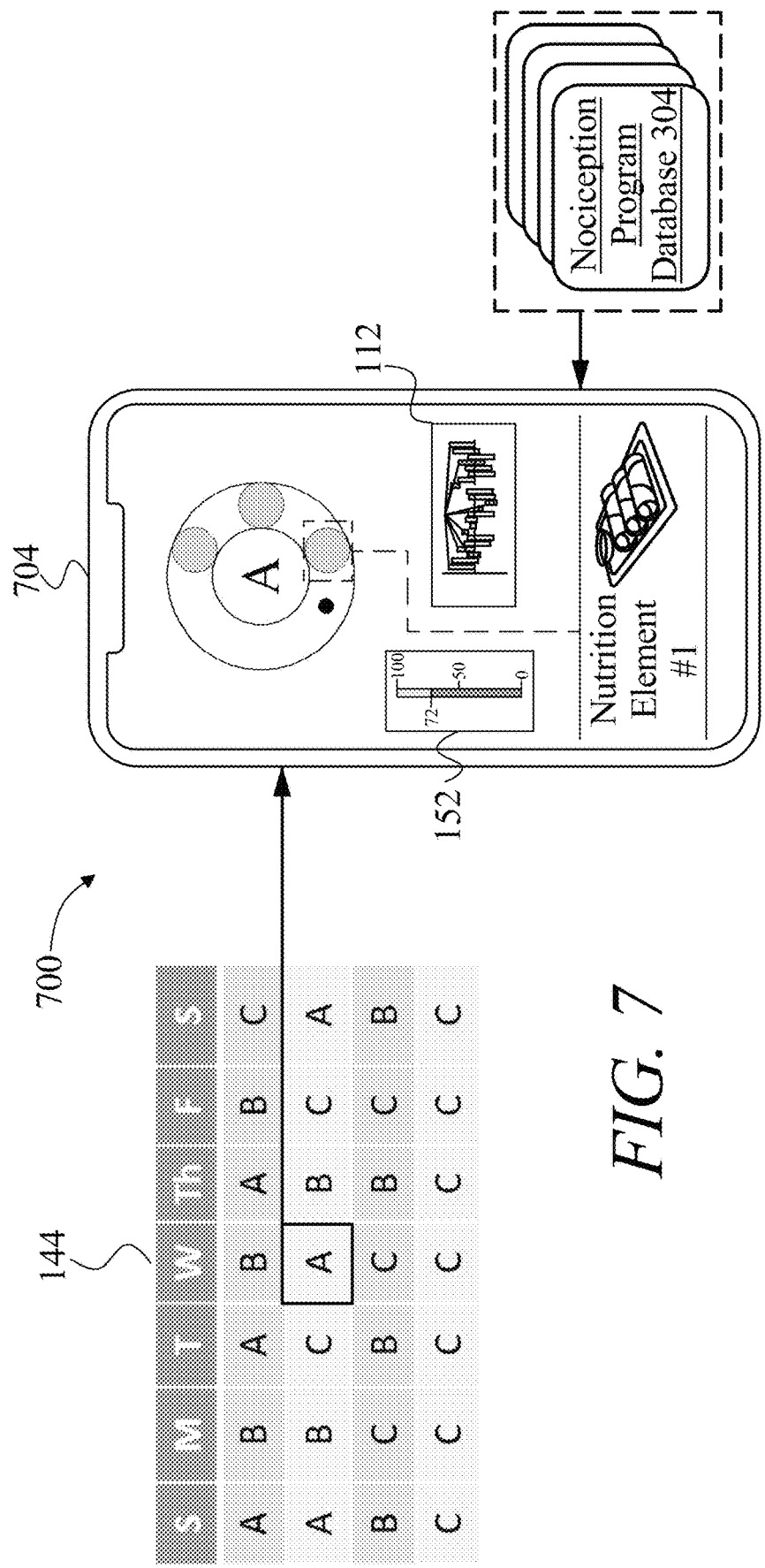
FIG. 7 is a diagrammatic representation of a client device.

Referring now to FIG. 7, a non-limiting exemplary embodiment 700 of a client device 704 is illustrated. Client device 704 may include computing device 104, a "smartphone," cellular mobile phone, desktop computer, laptop, tablet computer, internet-of-things (JOT) device, wearable device, among other devices. Client device 704 may include any device that is capable for communicating with computing device 104, nociception program database 304, or able to receive, transmit, and/or display, via a graphical user interface, nociception parameter 112, nutrition element 128, nociception nourishment program 144, nociception nourishment index 148, among other outputs from system 100. Client device 704 may provide a nociception parameter 112, for instance as a collection of metrics determined from nociception biologic 108 data. Client device 704 may provide nociception grouping 120 that was determined as a function of nociception classifier 124 and nociception parameter 112. Client device 704 may provide data concerning nutritional levels 140, including the levels of specific nutrients, nutrient ranges, nutrients to avoid, and the like. Client device 704 may link timing of foods to preemptive ordering interface for ordering a nutrition element 128, for instance and without limitation, through a designated mobile application, mapping tool or application, and the like, and a radial search method, or any other locating method, about a subject's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. Client device 704 may display nutrient elements 120 as a function of location and biological extraction data, for instance and without limitation, as described in the incorporated reference. Client device 704 may link nourishment consumption program 120 to a scheduling application, such as a 'calendar' feature on client device, which may set audio-visual notifications, timers, alarms, and the like, to assist subject in maintaining optimal nutritional levels 140.

Figure 8:
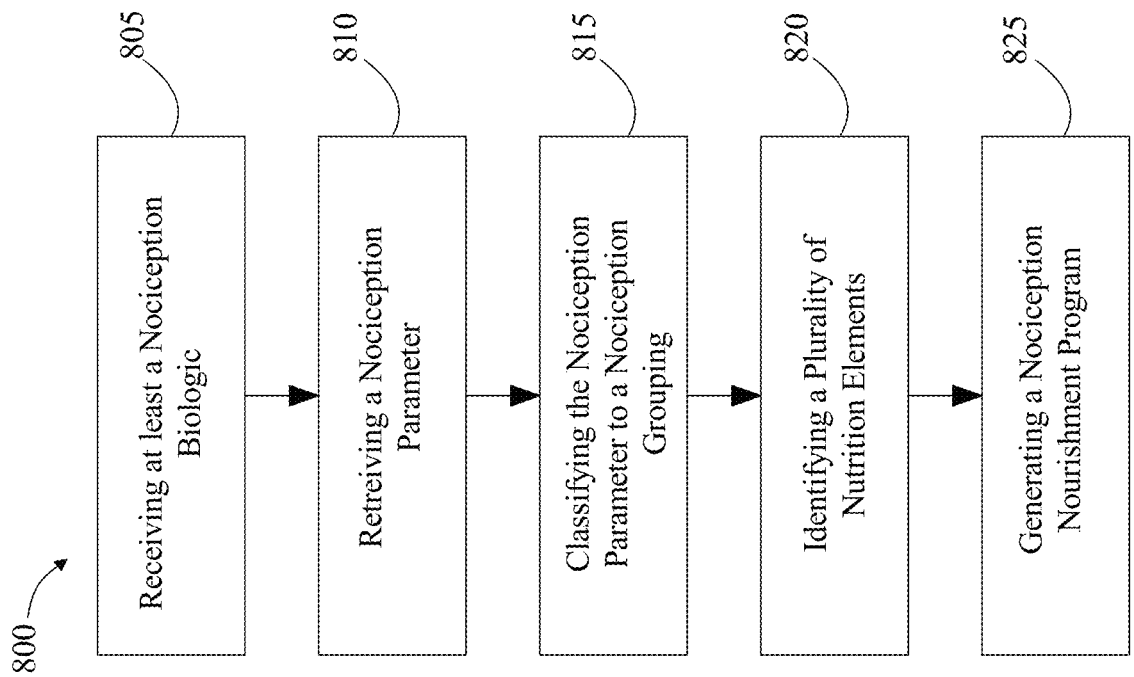
FIG. 8 is a block diagram of a workflow of a method for generating a nociception nourishment program.

Referring now to FIG. 8, an exemplary embodiment 800 of a method for generating a nociception nourishment program 144 is illustrated. At step 805, the method includes receiving, by a computing device 104, at least a nociception biologic 108 from a subject; this may be implemented, without limitation, as described above in FIGS. 1-7.

Still referring to FIG. 8, at step 810, method includes retrieving, by the computing device 104, a nociception parameter 112 related to the subject. Retrieving the nociception parameter 112 related to the subject may include training a nociception machine-learning model 116 with training data including a plurality of data entries correlating nociception biologics to nociception parameters and generating the nociception parameter 112 as a function of the nociception machine-learning model 116 and the at least a nociception biologic 108; this may be implemented, without limitation, as described above in FIGS. 1-7.

Continuing in reference to FIG. 8, at step 815, method includes classifying, by the computing device 104, the nociception parameter 112 to a nociception grouping 120. Classifying the nociception parameter 112 to a nociception grouping 120 may include training a nociception classifier 124 using a nociception classification machine-learning process and training data including a plurality of data entries of nociception parameter data from a subset of categorized subjects and classifying the nociception parameter 112 to the nociception grouping 120 using the nociception classifier 124. Classifying may include classifying the nociception parameter 112 to a nutrition-linked nociception disorder grouping; this may be implemented, without limitation, as described above in FIGS. 1-7.

Continuing in reference to FIG. 8, at step 820, method includes identifying, by the computing device 104, using the nociception grouping 120, a plurality of nutrition elements 128, wherein identifying the plurality of nutrition elements 128 includes generating a plurality of nutritional metrics 132 that aid in reduction of nociception as a function of the nociception grouping 120, determining a respective effect 136 of each nutritional metric 132 of the plurality of nutritional metrics on the nociception parameter 112, calculating at least a nutritional level 140 as a function of the respective effect 136 of each nutritional metric 132, wherein the at least a nutritional level 140 includes a nutrient amount intended to address the nociception parameter and identifying the plurality of nutrition elements 128 as a function of the at least a nutritional level 140. Determining a respective effect 136 of each nutritional metric 132 of the plurality of nutritional metrics 132 may include retrieving the respective effect 136 of each nutritional metric 132 on the nociception parameter 112 as a function of at least the nociception biologic 108. Calculating the at least a nutritional level 104 may include generating a nutrition machine-learning model according to the training data, wherein training data includes a plurality of data entries correlating the respective effect 136 of each nutritional metric 132 to a plurality of nutritional levels 140 for each nociception grouping 120 and calculating the at least a nutritional level 140 as a function of the nutrition machine learning model and the plurality of nutritional metrics 132. Identifying the plurality of nutrition elements 128 may include retrieving the plurality of nutrition elements 128 as a function of the nociception grouping 120; this may be implemented, without limitation, as described above in FIGS. 1-7.

Continuing in reference to FIG. 8, at step 825, method includes generating, by the computing device 104, a nociception nourishment program 144 using the plurality of nutrition elements 128. Generating the nociception nourishment program 144 may include generating a linear programming function with the at least the plurality of nutrition elements 128 wherein the linear programming function outputs at least an ordering of a plurality of nutrition elements 128 according to constraints from the nociception grouping 120 and the nutritional level 140. Nociception nourishment program 144 may include a nociception nourishment index 148. Generating the nociception nourishment program 144 nociception nourishment index 148 may include receiving nutritional input from a subject interaction with a client device 704, generating an indexing model 152 using training data including a plurality of data entries correlating the respective effect of each nutrition element in the nociception nourishment program on the nociception parameter and generating the nociception nourishment index 148 as a function of the indexing model 152 and the nutritional input.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
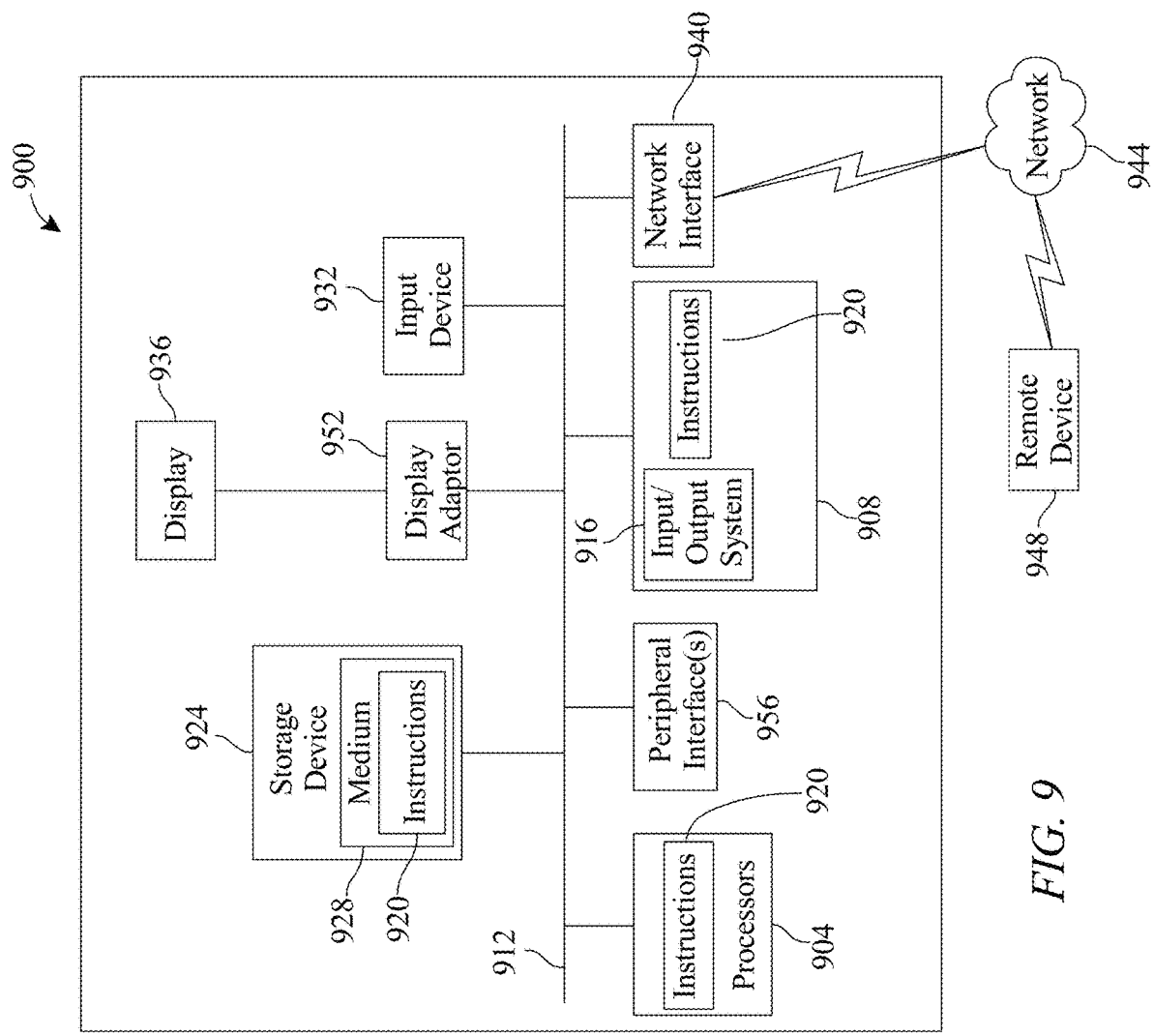
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, and the like) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, and the like) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for generating a nourishment program for nociception disorders, the system comprising:
   a computing device, wherein the computing device is configured to:
   retrieve a nociception parameter related to a subject;
   classify the nociception parameter to a nociception grouping;
   identify, using the nociception grouping, a plurality of nutrition elements, wherein identifying the plurality of nutrition elements includes:
   generating a plurality of nutritional metrics associated with reduction of nociception as a function of the nociception grouping;
   determining a respective effect of each nutritional metric of the plurality of nutritional metrics on the nociception parameter;
   calculating at least a nutritional level as a function of the respective effect of each nutritional metric, wherein the at least a nutritional level comprises a nutrient amount intended to address the nociception parameter; and
   identifying the plurality of nutrition elements as a function of the at least a nutritional level;
   modifying the plurality of nutrition elements as a function of a subject preference, wherein a subject preference comprises a constraint of at least one nutrition element of the plurality of nutrition elements; and
   generate a nociception nourishment program, which comprises a nociception nourishment index, using the modified plurality of nutrition elements, wherein generating the nociception nourishment index comprises:
   receiving nutritional input based on a subject interaction with a client device:
   generating an indexing model using training data including a plurality of data entries correlating the respective effect of each nutrition element in the nociception nourishment program on the nociception parameter; and
   generating the nociception nourishment index as a function of the indexing model and the nutritional input.

2. The system of claim 1, wherein retrieving the nociception parameter related to the subject further comprises:
   receiving at least a nociception biologic;
   training a nociception machine-learning model with training data including a plurality of data entries correlating nociception biologics to nociception parameters; and
   generating the nociception parameter as a function of the nociception machine-learning model and the at least a nociception biologic.

3. The system of claim 1, wherein classifying the nociception parameter to a nociception grouping further comprises:
   training a nociception classifier using a nociception classification machine-learning process and training data including a plurality of data entries of nociception parameter data from a subset of categorized subjects; and
   classifying the nociception parameter to the nociception grouping using the nociception classifier.

4. The system of claim 3, wherein classifying includes classifying the nociception parameter to a nutrition-linked nociception disorder grouping.

5. The system of claim 1, wherein determining a respective effect of each nutritional metric of the plurality of nutritional metrics further comprises retrieving the respective effect of each nutritional metric on the nociception parameter as a function of the at least a nociception biologic.

6. The system of claim 1, wherein calculating the at least a nutritional level further comprises:
   generating a nutrition machine-learning model according to the training data, wherein training data includes a plurality of data entries correlating the respective effect of each nutritional metric to a plurality of nutritional level for each nociception grouping; and
   calculating the at least a nutritional level as a function of the nutrition machine learning model and the plurality of nutritional metrics.

7. The system of claim 1, wherein identifying the plurality of nutrition elements further comprises retrieving the plurality of nutrition elements as a function of the nociception grouping.

8. The system of claim 1, wherein generating the nociception nourishment program further comprises generating a linear programming function with the at least the plurality of nutrition elements wherein the linear programming function outputs at least an ordering of a plurality of nutrition elements according to constraints from the nociception grouping and the nutritional level.

9. A method for generating a nourishment program for nociception disorders, the method comprising:

retrieving, by the computing device, a nociception parameter related to a subject;

classifying, by the computing device, the nociception parameter to a nociception grouping;

identifying, by the computing device, using the nociception grouping, a plurality of nutrition elements, wherein identifying the plurality of nutrition elements includes:

generating a plurality of nutritional metrics associated with reduction of nociception as a function of the nociception grouping;

determining a respective effect of each nutritional metric of the plurality of nutritional metrics on the nociception parameter;

calculating at least a nutritional level as a function of the respective effect of each nutritional metric, wherein the at least a nutritional level comprises a nutrient amount intended to address the nociception parameter; and identifying the plurality of nutrition elements as a function of the at least a nutritional level;

modifying the plurality of nutrition elements as a function of a subject preference, wherein a subject preference comprises a constraint of at least one nutrition element of the plurality of nutrition elements; and generating, by the computing device, a nociception nourishment program which comprises a nociception nourishment index, using the plurality of modified nutrition elements, wherein generating the nociception nourishment index comprises:

receiving nutritional input based on a subject interaction with a client device;

generating an indexing model using training data including a plurality of data entries correlating the respective effect of each nutrition element in the nociception nourishment program on the nociception parameter; and generating the nociception nourishment index as a function of the indexing model and the nutritional input.

10. The method of claim 9, wherein retrieving the nociception parameter related to the subject further comprises:

receiving at least a nociception biologic;

training a nociception machine-learning model with training data including a plurality of data entries correlating nociception biologics to nociception parameters; and generating the nociception parameter as a function of the nociception machine-learning model and the at least a nociception biologic.

11. The method of claim 9, wherein classifying the nociception parameter to a nociception grouping further comprises:

training a nociception classifier using a nociception classification machine-learning process and training data including a plurality of data entries of nociception parameter data from a subset of categorized subjects; and classifying the nociception parameter to the nociception grouping using the nociception classifier.

12. The method of claim 11, wherein classifying includes classifying the nociception parameter to a nutrition-linked nociception disorder grouping.

13. The method of claim 9, wherein determining a respective effect of each nutritional metric of the plurality of nutritional metrics further comprises retrieving the respective effect of each nutritional metric on the nociception parameter as a function of at least the nociception biologic.

14. The method of claim 9, wherein calculating the at least a nutritional level further comprises:

generating a nutrition machine-learning model according to the training data, wherein training data includes a plurality of data entries correlating the respective effect of each nutritional metric to a plurality of nutritional levels for each nociception grouping; and calculating the at least a nutritional level as a function of the nutrition machine learning model and the plurality of nutritional metrics.

15. The method of claim 9, wherein identifying the plurality of nutrition elements further comprises retrieving the plurality of nutrition elements as a function of the nociception grouping.

16. The method of claim 9, wherein generating the nociception nourishment program further comprises generating a linear programming function with the at least the plurality of nutrition elements wherein the linear programming function outputs at least an ordering of a plurality of nutrition elements according to constraints from the nociception grouping and the nutritional level.

* * * * *